United States Patent [19]
Boyer et al.

[11] Patent Number: 5,907,493
[45] Date of Patent: May 25, 1999

[54] PHARMACEUTICAL DISPENSING SYSTEM

[75] Inventors: Joseph H. Boyer; James P. Boyer, both of Johnson City, N.Y.

[73] Assignee: Innovation Associates, Inc., Johnson City, N.Y.

[21] Appl. No.: 08/792,208

[22] Filed: Jan. 31, 1997

[51] Int. Cl.[6] ...................................................... G06F 17/00
[52] U.S. Cl. ............................... 364/479.01; 364/479.11; 364/479.14; 364/478.01
[58] Field of Search ......................... 364/479.01, 479.02, 364/479.06, 479.07, 479.11, 479.12, 479.13, 479.14, 478.01, 478.08, 478.07; 221/75, 13, 200, 7, 2, 258, 9; 53/53, 54, 55

[56] References Cited

U.S. PATENT DOCUMENTS

| | | | |
|---|---|---|---|
| 4,542,808 | 9/1985 | Lloyd, Jr. et al. | 364/479.12 |
| 4,847,764 | 7/1989 | Halvorson | 221/2 |
| 5,014,875 | 5/1991 | McLaughlin et al. | 221/2 |
| 5,205,436 | 4/1993 | Savage | 364/479.06 |
| 5,208,762 | 5/1993 | Charhut et al. | 364/478.04 |
| 5,267,174 | 11/1993 | Kaufman et al. | 364/479.12 |
| 5,272,321 | 12/1993 | Otsuka et al. | 364/479.06 |
| 5,292,029 | 3/1994 | Pearson | 221/2 |
| 5,303,844 | 4/1994 | Muehlberger et al. | 221/75 |
| 5,337,919 | 8/1994 | Spaulding et al. | 221/2 |
| 5,377,864 | 1/1995 | Blechl et al. | 221/2 |
| 5,502,944 | 4/1996 | Kraft et al. | 364/479.12 |
| 5,720,154 | 2/1998 | Lasher et al. | 53/411 |

*Primary Examiner*—Joseph E. Valenza
*Assistant Examiner*—Wonki Park
*Attorney, Agent, or Firm*—Salzman & Levy

[57] ABSTRACT

The present invention features a pharmaceutical dispensing system including a plurality of standardized or universal-type cells disposed in a large array called a module. One or more modules may be disposed in a given pharmacy, and one or more pharmacies may be monitored by a central computer. The system for filling prescriptions includes a graphical interface processing system for monitoring operations of each cell, wherever located, and for sequentially and interactively prompting an operator to perform appropriate; predetermined steps. The system for filling prescriptions sequentially prompts a technician or operator to perform predetermined steps, dependent upon verification of the completion of a prior or previously completed step in the sequence. In a semi-automatic mode, the pharmacist is directed, by suitable prompts on the computer display screen, as to the necessary steps and locations in filling each prescription. The main computer stores information of a plurality of drugs in predetermined, separately-addressable cells, and arranges that information to provide optimum efficiency of pharmacy operations, dependent upon certain parameters: (1) a proximity to a predetermined packaging/shipping location; (2) the probability of future drug access at a predetermined inventory storage location; (3) the size of separately-addressable storage locations; and (4) the location of confusingly similar drugs or dosages. The separately-addressable storage locations in inventory have adjustable shelves.

25 Claims, 24 Drawing Sheets

PHARMACEUTICAL DISPENSING SYSTEM

RELATED PATENT APPLICATION

This patent application is related to copending patent application, Ser. No. 08/759,279 filed Dec. 2, 1996, entitled, SYSTEM FOR DISPENSING PILLS, assigned to a common assignee, and hereby incorporated by reference.

FIELD OF THE INVENTION

The present invention relates to a computer controlled and computer directed pharmaceutical dispensing system, and, more particularly, to an automated pharmaceutical dispensing system with a main, or centralized workstation monitoring an array of modules, each having a plurality of cells bulk loaded with a specific pill, tablet, or capsule distinctive to its express address. Each cell in each module may be accessed manually by an operator or may be part of an automated system that counts and dispenses a desired amount of the pharmaceutical needed to fill a given prescription.

BACKGROUND OF THE INVENTION

The pharmaceutical dispensing system of this invention is used to fill prescriptions under centralized computer control. The system monitors operations of each module of a pharmacy, or a number of pharmacies, and sequentially and interactively prompts one or more operators to perform appropriate, predetermined steps. The workstation includes a graphical interface that displays the monitored status of a plurality of prescriptions, thereby monitoring an array of cells in an array of modules. The centralized workstation graphically displays the status of each drug being dispensed by each cell in the array of modules.

Each module comprises predetermined, separately-addressable cells (storage locations) in the workstation inventory, each cell storing a particular drug.

Information with respect to the prescription to be filled, and its urgency, is sent to a central or main computer. The information for filling the prescriptions is monitored by the main computer, and the status of the drugs is graphically displayed. The system for filling prescriptions sequentially prompts a technician or operator to perform predetermined steps. The sequential prompting of the operator to perform each predetermined step may be dependent upon verification of the completion of a prior or previously completed step or steps in the sequence.

The pharmaceutical dispensing system also requires that predetermined steps can be performed only by an identified operator. The identification of the operator can be provided by a barcode that is part of the I. D. badge of the operator. The barcode is scanned to allow the operator access to the dispensing system, and to verify completion of each task. The main computer monitors the activity of the operator and existing inventories. The main computer of the system stores information of a plurality of drugs in predetermined, separately-addressable storage locations in inventory, and arranges that information to provide optimum efficiency of pharmacy operation.

The field of pill dispensing features many different mechanisms that are designed to recognize, sort, and count pills and capsules of all types and sizes. The major problem with many of these devices is reliability. In order for one apparatus to properly sort or recognize different pills by size and shape, it has often been necessary to modify the design of the dispenser to fit each particular shaped or sized pill. Often, adjustments must be performed to the machine during operation. Such changes greatly inhibit the use of such devices in automated, or semiautomated, or continuously run facilities. The pharmaceutical dispensing system of the present invention suggests a new apparatus that is reliable, and which can handle a wide variety of pills, tablets, and capsules without requiring adjustments or modification to the basic design. As used herein, the term "pills" is to be understood to include pills, tablets, capsules and all other containers for, and shapes of, pharmaceuticals to be swallowed, chewed or dissolved by the end user.

The pharmaceutical dispensing system of the present invention comprises a standardized or universal type module with a plurality of individual cells, each of which can be easily loaded through a hopper, capable of being filled with any type of pills, tablets and capsules of varying size and shape. The cell dispenser has a simple screw-type feed and dispensing mechanism that can operate at different speeds to accommodate different pills. A multiplicity of cells can be arrayed in one of a number of modules that is computer controlled. The speed of each dispensing mechanism is controlled by a main computer, so that each cell can be individualized for a specific pill, tablet, or capsule. In this manner, a wide range of pills can be dispensed as needed for a pharmaceutical facility. The computer at the pharmaceutical facility communicates with the main computer, and informs the main computer what prescriptions need filling. The main computer keeps track of all of the prescriptions, and establishes priorities based on pharmacy inputs.

The system comprises a large bank of dispensing cells that are more cost effective and compact than existing pill dispensing apparatuses. Each cell in the array is able to dispense and count accurately at a relatively high speed, resulting in increased overall system throughput. The dispensing cell design allows for its use in banks or arrays, which are compact enough to allow a single operator to handle 200 or more dispensers from a single location. The form of the device will also allow its use in an automated dispensing or prepackaging facility, allowing such facilities to be configured into economical systems.

As aforementioned, the pharmaceutical system provides a basic design that can handle a complete range of tablet or capsule sizes and shapes. This is accomplished without requiring different mechanical operation, or mechanical adjustment. The cells feature a basic design that is controlled electronically, as described in the aforementioned, copending patent application, Ser. No. 08/759,279. The computer is programmable to provide different drive voltages that adjust the timing and operation of the mechanism, which in turn sets the device to operate specifically for a particular pill.

The mechanism of each cell features a sloped tube containing a helical interior ridge. The tube is set at an angle to the horizontal. The sloped tube with its helical ridge is rotated, causing pills fed to the mouth of the tube to move upwardly along the tube against gravity, thereby becoming separated either individually, or into smaller groups. As the pills reach the end of the tube, they are individually separated, and can be accurately dispensed from the end thereof. The falling pills are then detected individually by photodetector cells,.and are thereby reliably counted. The computer controlling the dispensing operation is programmed to recognize a double feed, or a broken, fragmented pill.

Screw feed separation and photoelectric counting are known in the art. U.S. Pat. No. 5,213,232, issued to KRAFT et al, discloses an apparatus for dispensing single units such as pills. A generally circular, walled container has a bottom for holding the units and a discharge area located distally from the bottom for receiving the single units and for discharging them upon manual rotation. A helical spiraled rib member is located on the circular walled container for creating, during rotation, a continuously variable inclined surface along the helical spiraled rib member and the circular walls of the container. In addition to requiring the bottom (making it impossible to incorporate in a system with a hopper), the system is not adapted to be automatically advanced. The dispensing cell of the present invention features significant improvements over previous existing concepts, however, such that the basic simplicity and reliability is retained, but speed and accuracy are enhanced.

It is the basic simplicity that is the key to the maintenance-free reliability sought. The incorporated improvements to the basic design provide significant changes in operational features, speed, and accuracy. The cell retains simplicity, while being part of a sophisticated pharmaceutical dispensing network.

The computer controlling the dispensing mechanism stops the rotation of the dispensing tube when the number of pills counted by the device approaches the number desired for a given dispensing count. Afterward, the computer intermittently rotates the tube through a small angle, waiting between successive intermittent jogs for a signal from the photodetector that the final pill in the count has dropped therethrough. This intermittent rotation at the end of the dispensing cycle, reduces the tendency of multiple pills from dropping from the end of the tube. In this fashion, the computer control ensures that an accurate final count of pills will be obtained. The size of the incremental angle and the duration of the wait are adjusted in software to be optimum for the size of the pills being dispensed. In this way, the only adjustment required to accommodate the different sizes of pills is accomplished in software that affects only the helix rotation. No mechanical modifications or adjustments are required for this purpose.

SUMMARY OF THE INVENTION

In accordance with the present invention, there is provided a pharmaceutical dispensing system including a plurality of standardized or universal-type cells disposed in a large array called a module. One or more modules may be disposed in a given pharmacy, and one or more pharmacies may be monitored by a central computer.

The system for filling prescriptions includes a graphical interface processing system for monitoring operations of each cell, wherever located, and for sequentially and interactively prompting an operator to perform appropriate, predetermined steps. The status of each drug being dispensed is monitored. The cells in the array each store a particular drug, and each cell has a predetermined address in the inventory. Information from each pharmacy with respect to the prescription to be filled, and its status, is sent to a central or main computer. The information for filling the prescription is monitored by the main computer, and the status of the drugs is graphically displayed. The system for filling prescriptions sequentially prompts a technician or operator to perform predetermined steps, dependent upon verification of the completion of a prior or previously completed step in the sequence. The pharmaceutical dispensing system also requires that predetermined steps can be performed only by an identified operator. The identification of the operator can be provided by a barcode that is part of the I. D. badge of the operator. The main computer stores information of a plurality of drugs in predetermined, separately-addressable cells, and arranges that information to provide optimum efficiency of pharmacy operations, dependent upon certain parameters: (1) a proximity to a predetermined packaging/shipping location; (2) the probability of future drug access at a predetermined inventory storage location; (3) the size of separately-addressable storage locations; and (4) the location of confusingly similar drugs or dosages. The separately-addressable storage locations in inventory have adjustable shelves.

BRIEF DESCRIPTION OF THE DRAWINGS

A complete understanding of the present invention may be obtained by reference to the accompanying drawings, when considered in conjunction with the subsequent detailed description, in which:

FIG. 1b depicts a schematic of the automated pharmaceutical system of this invention utilizing the method shown in FIG. 1a;

DESCRIPTION OF THE PREFERRED EMBODIMENT

Generally speaking, the invention features a pharmaceutical dispensing system and method that is fully- or semi-automated, and which comprises a plurality of standardized pill dispensing cells arranged in one or more modules that are controlled and monitored by a computer. Each dispensing cell uses a screw feed mechanism that will dispense pills of all shapes and sizes. The screw feed mechanism is designed to change the material flow through the screw feed area, or flow zone, to effect singulation (i.e., a single file configuration of flow) of the pills. This singulation of the pills passing through the screw feed zone is accomplished by interrupting, delaying, and otherwise urging the pills backwardly into the pill mass. The pill mass features a bulk loading of pill materials from a storage device, such as a hopper. The pills enter at the input end, or mouth of a screw feed tube. A photodetector disposed at the output, or dispensing end of the screw feed tube counts the number of pills falling off the edge of the tube, and sends a signal to a microprocessor. The microprocessor generally controls the rate at which the screw feed tube rotates, which rotation depends upon the size and shape of the pills, tablets, or capsules passing therethrough. After the correct amount of pills has been counted, the pharmacist is directed to place a vial of a given size under the dispensing chute of the cell, and affix a printed label. The system may operate in a completely automated mode, thus preventing any mistakes. In a semi-automatic mode, the pharmacist is directed, by suitable prompts on the computer display screen, as to the necessary steps and locations in filling each prescription. The pharmacist can also override the system in case of a rush order, or emergency. All the procedures are checked by proper scanning of barcoded information.

Figure 1A:
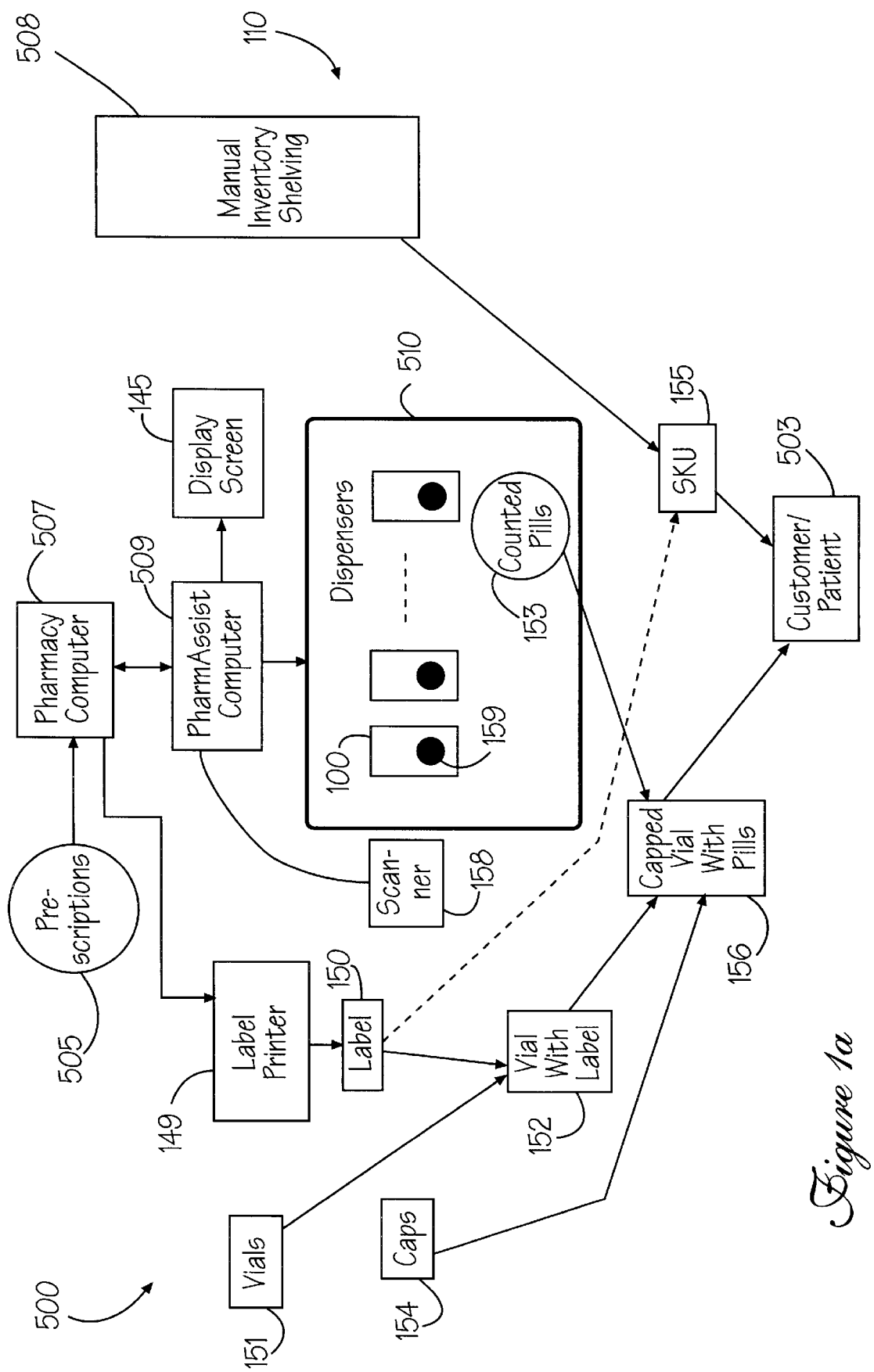
FIG. 1a shows a block diagram of the pharmaceutical dispensing method of this invention.

Referring to FIG. 1a, a block diagram of the dispensing method 110 of the system 500 of this invention is shown. Prescriptions 505 are manually entered into a pharmacy computer 507, which currently exists in most pharmacies. A label printer 149 is typically connected to the pharmacy computer 507, and prints a label 150, which is to be placed on a vial 151 or other container 155 containing the filled prescription.

In the present method, the dispenser controller or main computer 509 is normally equipped with a video display screen 145. Computer 509 connects to the automatic dispensing cells 100 in array 510. Each cell 100 counts and dispenses a number of pills 153 of a specific pharmaceutical, which comprises a specific shape and size.

Figure 1B:
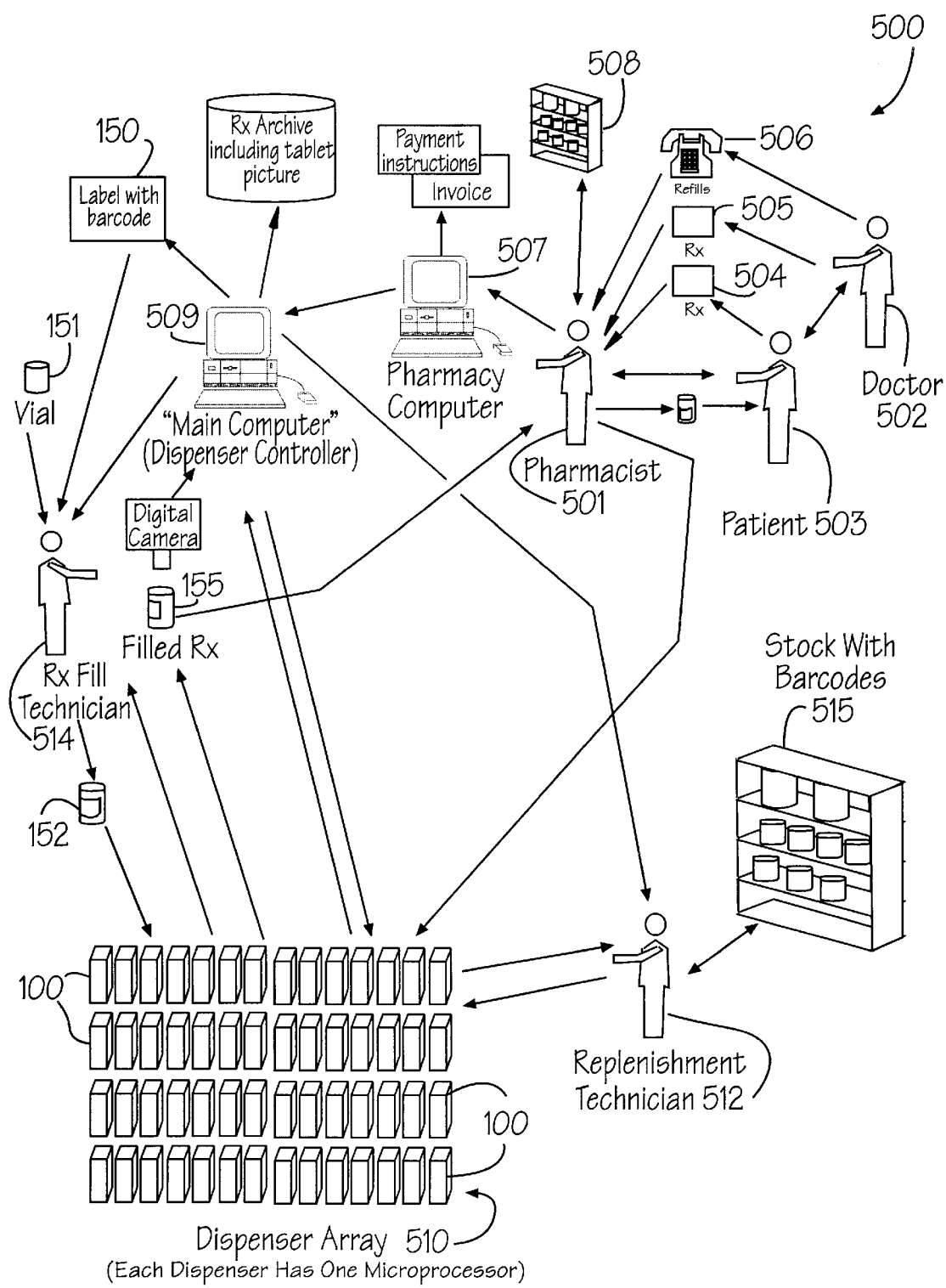

Now referring also to FIG. 1b, a schematic diagram of the automated system 500 of this invention is illustrated. The system 500 illustrates a pharmacist 501 at a particular pharmacy that receives various prescriptions from one or more doctors 502, who prescribe particular medicines to one or more patients 503. The prescription(s) is presented to the pharmacist 501 via a written prescription 504 presented by the patient 503, or via a prescription 505 provided in writing, by telephone, or by electronic transmission (e.g., fax, e-mail) directly from the doctor 502. Therefore, doctor 502 can also phone the pharmacy via telephone 506 to authorize refills for patient 503. The pharmacist 501 enters information of each individual prescription into the pharmacy computer 507. The pharmacist 501 may in some cases fill a prescription manually from his or her own stock 508. The pharmacy computer 507 sends the information of the pharmacy prescriptions to be filled, to a centralized workstation having a main computer 509. The workstation is connected to one or more arrays or banks 510 of standardized dispensing cells 100. Each dispensing cell 100 in the array 510 is controlled by its own microprocessor, not shown. Each cell 100 contains a specific drug to fill a specific prescription order.

The workstation comprises technicians or operators 512 and 514, respectively. Replenishment operator 512 bulk loads each dispensing cell 100 with pills from inventory stock 515. In alternate embodiments, loading may be performed from the front of cell 100. Filling operator 514 works in front of the array 510, and retrieves each prescription as it is filled. Filling technician 514 is instructed by the main computer 509 as to the procedural steps necessary to fill each prescription. The main computer 509 also informs the replenishment technician 512 what cells 100 need repair, maintenance, or refilling.

Either the main computer 509 or pharmacy computer 507 prints a barcoded label 150 for each dispensed drug, which label must be applied to the vial of each dispensed drug.

Each operator 512 and 514 must scan his or her identification badges with a barcode scanner or wand, in order to gain access to the main computer 509, and to verify each operation. The main computer 509 monitors inventory and prioritizes each prescription based upon urgency and pharmacy operations. The main computer 509 displays the information and provides sequential instructions (prompts) with respect to the filling of each prescription. The complete operation of the pharmaceutical dispensing system of this invention will become more apparent with reference to the detailed description described hereinafter.

In operation, printed label 150 is attached to a vial 151, resulting in a labeled vial 152. Label 150 is then scanned with a barcode scanner 158 (FIG. 1a), which reads back the prescription identification number to computer 509. If the number is correct, a ready light 159 (FIG. 1a) on dispenser array 510 will light, directing the filling technician or pharmacist 514 to the correct cell dispenser 100. Labeled vial 152 is then placed under the correct dispenser 100 and receives a counted number of the correct pills 153. A cap 154 is the n applied and the completed prescription 156 is delivered to the customer or patient 503. Alternatively, a packaged product 155 may be selected from shelves 148 under instructions from computer 509 and label 150 is applied directly to package 155.

All of these manual operation s are directed from dispenser controller main computer 509 through instructions or prompts appearing on video display screen 145.

Figure 1C:
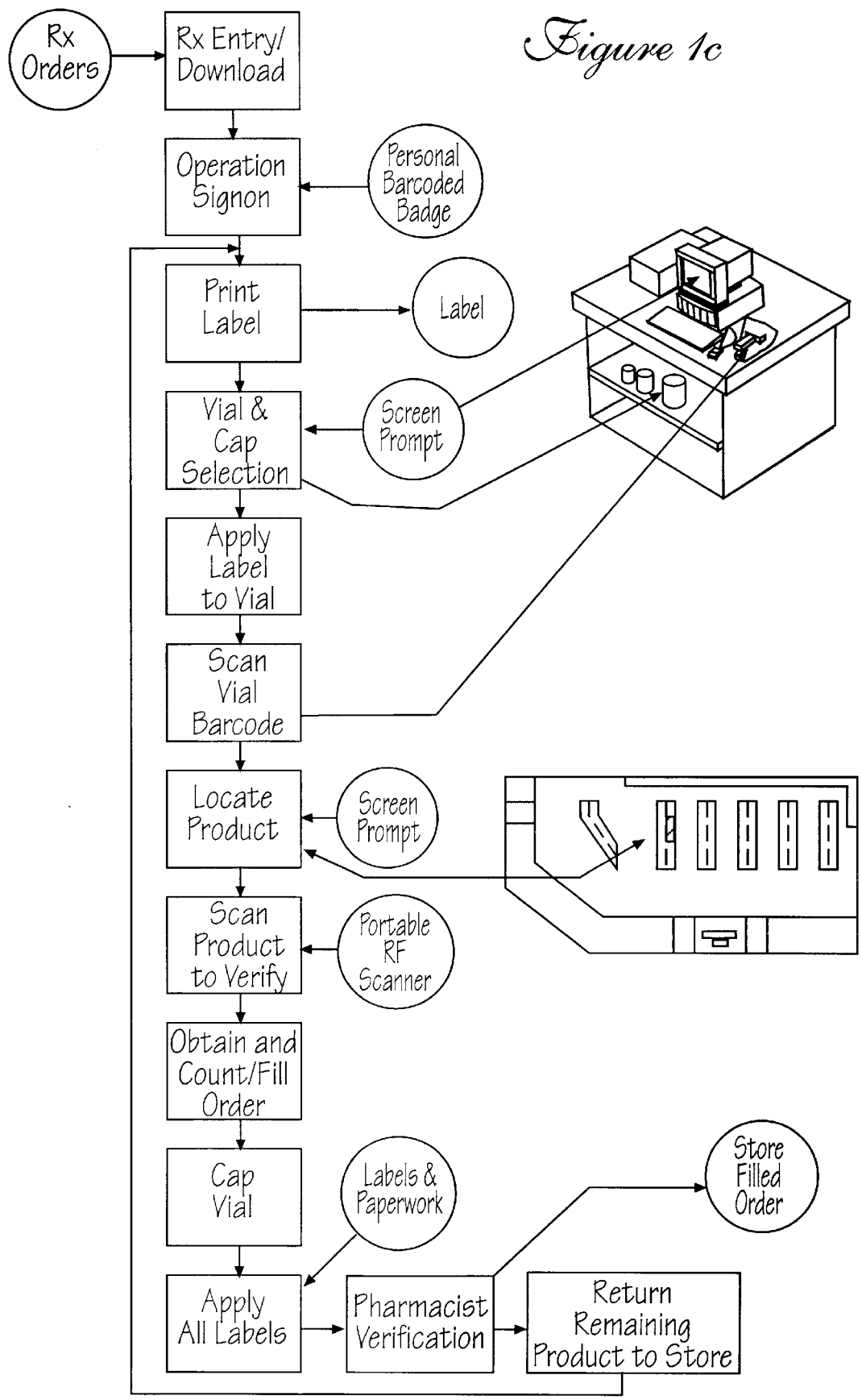
FIG. 1c shows a flowchart for manual and semiautomatic prescription fulfillment, prompted and monitored by the inventive system.

Referring now to FIG. 1c, there is shown a flowchart for manual and semi-automatic prescription fulfillment. As can be seen from this FIGURE, once a given prescription or request for a pharmaceutical is received by the system and an operator signs on to work as a fulfillment technician 514 (FIG. 1b), the fulfillment steps proceed in a serial manner. Specifically, a prescription bottle label is printed, a vial and cap are identified by the system and are selected by the operator, who applies the printed label to the vial and then scans the barcode thereon. Once the system prompts the operator to locate the pharmaceutical product, by actually and graphically identifying its location in the pharmacy, the operator scans a barcode at the appropriate location for verification, before obtaining the quantity of the product specified and counted out by the system. The basic operation is repeated when a new label is printed for the next prescription in the queue.

Figure 1D:
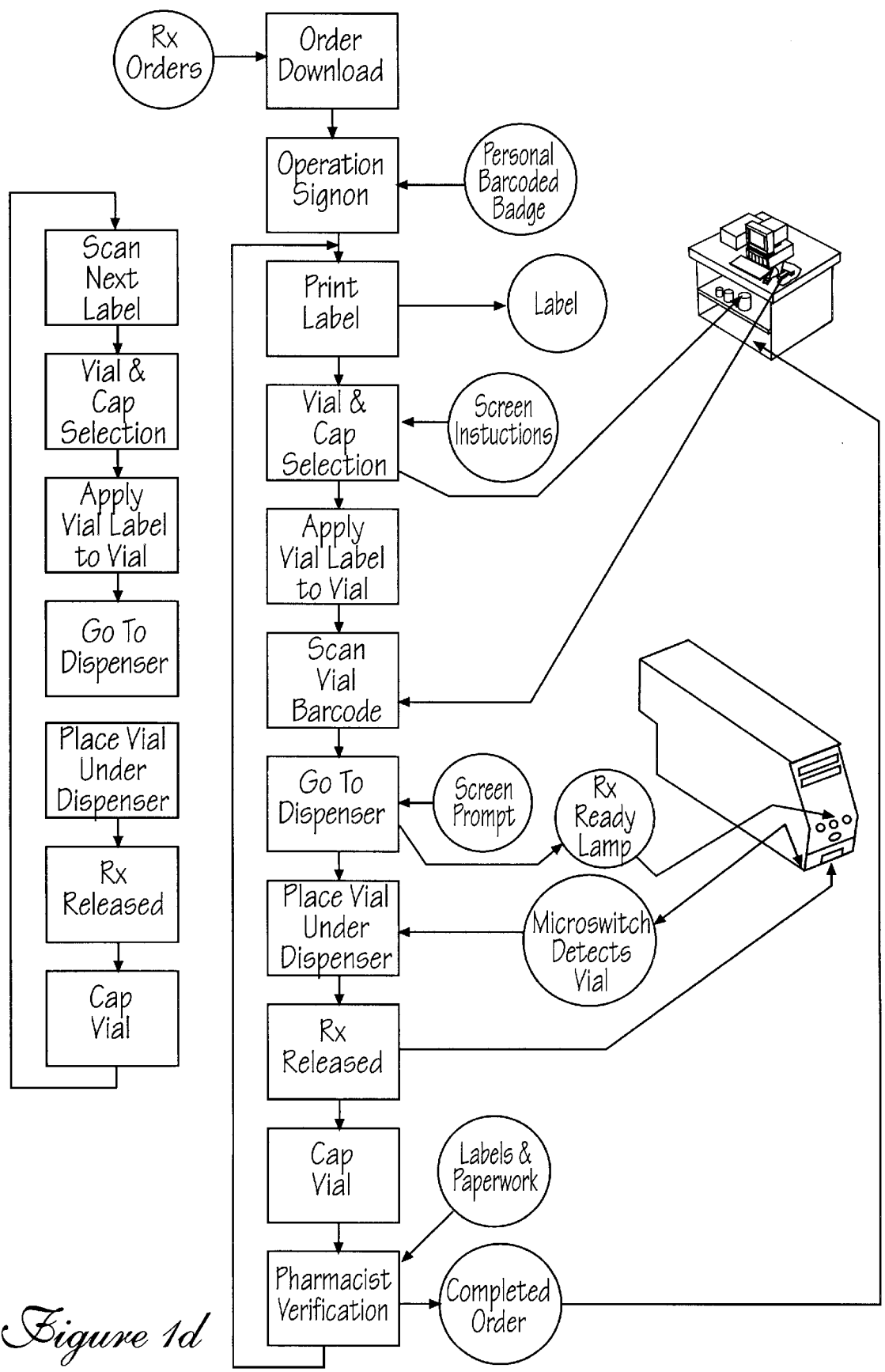
FIG. 1d shows a flowchart of automatic prescription fulfillment monitored by the inventive system.

Referring now also to FIG. 1d, there is shown a flowchart of automatic prescription fulfillment, monitored by the system. The procedure for automatically fulfilling prescriptions is quite similar to that procedure described hereinabove, with reference to FIG. 1c. The main difference between manual and automatic fulfillment, as can be seen by this FIG. 1d, is the presence and use of a dispenser, beneath which the appropriate vial is placed by an operator.

Also shown in FIG. 1d is an alternate process, used when labels are preprinted. In this batch mode of operation, labels are still affixed to appropriate vials by an operator, after which the operator approaches a suitable dispenser, places the vial beneath it, and then places a cap on the vial.

Figure 1:
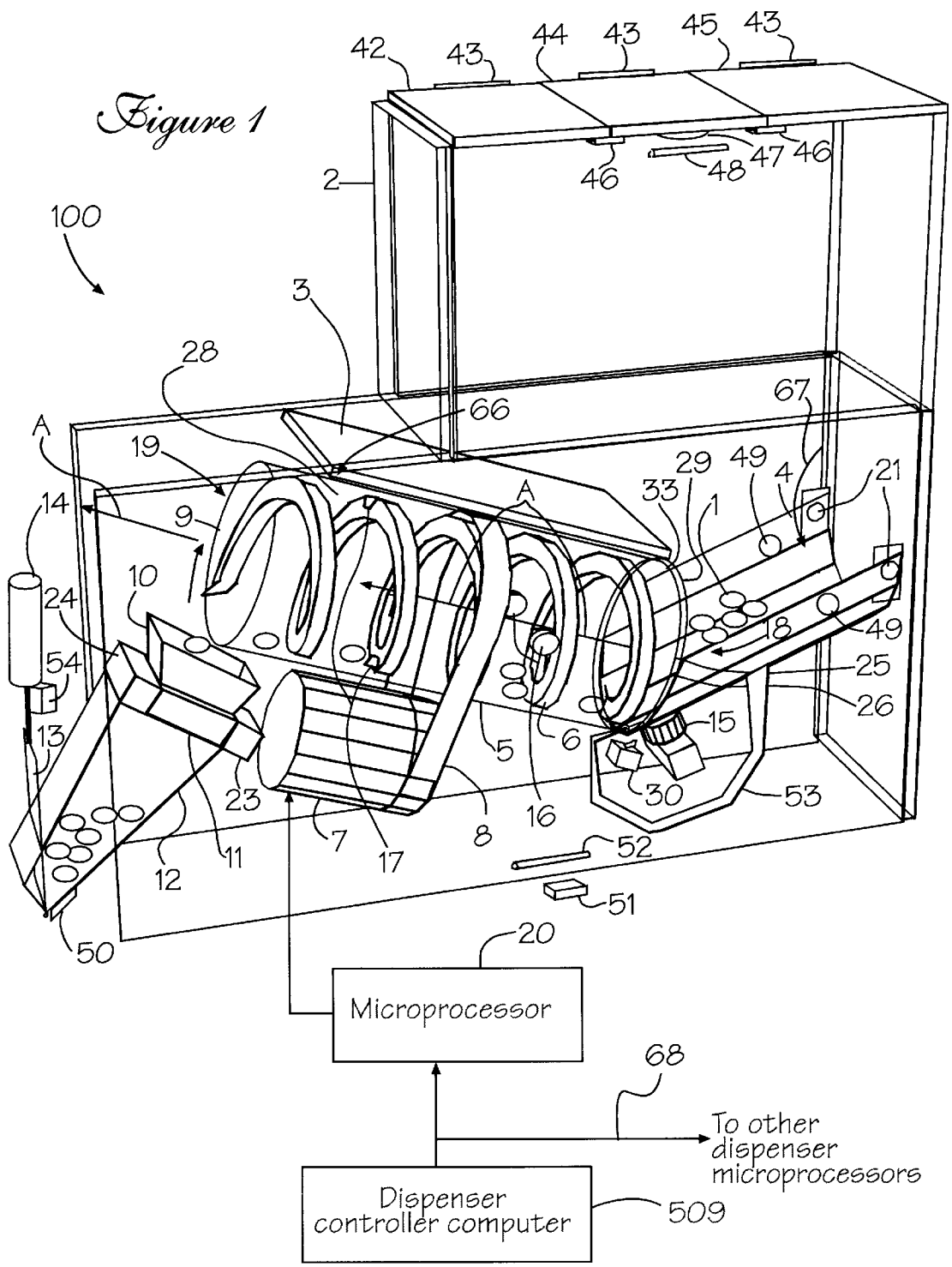
FIG. 1 illustrates a perspective, schematic view of the pill dispensing cell used in the automated pharmaceutical dispensing system of this invention.

Now referring to FIG. 1, a typical dispensing cell 100 is illustrated. The dispensing cells 100 each comprise a hollow tube 5 which is equipped with an interior helical ridge 6, hereinafter referred to as helix 6. The helix 6 is rigidly connected to the inside wall of the hollow tube 5. Tube 5 is inclined to the horizontal nominally between 10 and 30 degrees to the horizontal axis. The dispensing end 19 of the mechanism is disposed vertically above the input end, or mouth 18 of tube 5, such that tube 5 is inclined towards the dispensing end 19. The incline of tube 5 defines a central, longitudinal, or pill flow axis, as shown by arrows A. The tube 5 can be rotated in either direction, clockwise or counterclockwise, about the central, longitudinal axis A. A motor 7 drives a belt 8 that encircles tube 5. Motor 7 can be driven in either direction, clockwise or counterclockwise, by signals sent from a microprocessor 20. The belt is in frictional engagement with tube 5, such that it will cause the tube 5 to rotate, as the belt 8 is rotationally driven by motor 7. As -tube 5 rotates, the helix 6 transports the pills 1 up the inside wall of the elongated incline of tube 5.

A stationary collar 9, of the same inside and outside diameters as tube 5, is positioned across a gap 66 at the upper end of tube 5. The collar 9 is coincident with the central, longitudinal, axis of tube 5. The tube 5 and collar 9 are slightly separated by a gap 66, such that the stationary collar is fixed, while the tube 5 is caused to rotate. Helix 6 extends beyond tube 5, across gap 66, and into stationary collar 9. The helix 6 being attached to the tube 5 will therefore rotate within stationary collar 9, thus transporting pills 1 up through collar 9, and out the dispensing end 19.

As pills 1 are pushed to the lip-of collar 9, they fall off collar 9, and down through the funnel 10, through a photo-detector 11, and into the collection chute 12. Pills 1 are sensed by photodetector 11, which sends a signal to the microprocessor 20 for each sensed pill 1, via line 65. The microprocessor 20 processes the signals from photodetector 11, and keeps a running count of the total. Pills 1 are held in the collection chute 12 by vertically movable door 13, which can be raised by solenoid 14. The pills 1 fall out of the collection chute 12 through a dispensing spout 50 and into a hand-held vial, not shown, when door 13 is raised by solenoid 14.

The pills 1 are fed to tube 5, via the hopper 2. The hopper 2 is shaped like a box, having an opening at the bottom that empties onto a plate 3. The side walls of the hopper define a box in which a mass of pills, tablets, or capsules are fed to the tube 5. A trough 4 disposed below the plate 3, receives the pills 1 that slide down the plate 3 or which drop directly from hopper 2. The trough 4 delivers pills 1 to the mouth 18 of the rotating, hollow tube 5 containing the helix 6.

To facilitate pushing the last pill off the lip 22 of the collar 9, the helix 6 is bent at its tip 39. The bend in the tip 39 is in the direction of the central, longitudinal axis A of the helix. The pitch, or coil-to-coil distance, of the helix is effectively increased over the length of tip 39.

Figure 2:
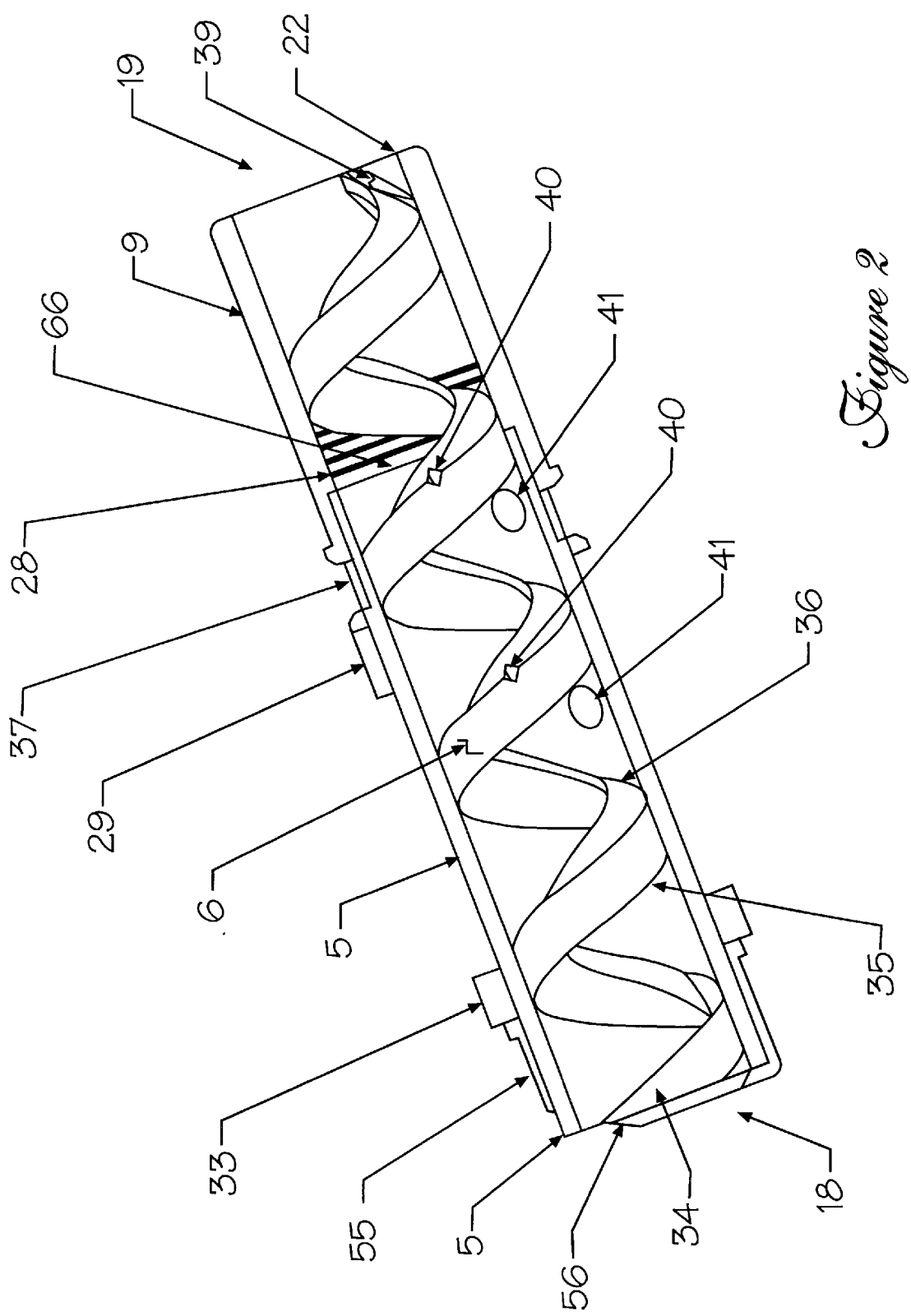
FIG. 2 depicts a sectional view of the rotatable helix-tube and adjacent stationary collar of the dispensing mechanism shown in FIG. 1.

It will be observed that tube 5 (FIG. 2) is supported at its input end 18 by bearing ring 55, in which tube 5 is free to rotate. A notch 56 in bearing ring 55 exposes the edge of tube 5, so that its rotation will cause pills from trough 4 (FIG. 1) to move as they contact the lip of the tube 5. This movement will provide enough agitation to the pill mass disposed at the input end 18, to assist in the flow of the pill mass into tube 5.

The photodetector 11 (FIG. 1) has a light source 23 on one side, and an array of photosensors 24 on the other side. As a pill 1 falls through detector 11, the light from light source 23 is blocked to at least one of the photosensors 24, and the pill 1 is detected, causing a signal to be sent to the microprocessor 20, which keeps a running count of the pills 1 falling into funnel 10. Microprocessor 20 performs an analysis on the photodetector 11 signal. The wave shape of the signal will determine whether a full or fragmented pill 1 has been sensed. Pill fragments are eliminated from the microprocessor count. Likewise, a double passage of pills 1 will be sensed by the photodetector 11, and the wave shape of the signal will enable the microprocessor 20 to ascertain that two pills 1 have overlapped. In such a case, the microprocessor will record a double count.

Vibration is optionally provided to the tube 5 in order to prevent bridging in the hopper area for certain pills and capsules. Vibration is provided to the tube 5 by the ridged, or serrated cam 33, that imparts a striated rotation. In other words, the rotation is somewhat bumpy, and this rotational bumpiness jiggles the pills as they move up the hollow tube 5. Cam 33 bears on, and transfers vibration to, plate 3. This causes pills disposed upon the plate to fall into trough 4. Cam 33 also imparts vibration to lever 53 which is attached-to chute 4, and therefore, also vibrates trough 4.

In addition to vibration at the inlet, the dispensing system 100 features another means to prevent the pills from jamming at the interface between chute 4, and the inlet portion 18 of the tube 5. The chute 4 is supported by a compression spring 15 at the inlet 18 interface with tube 5. On the other end, chute 4 is rotationally supported by two pivots 21. In the event that a pill jam occurs at the point where helix 6 picks up the pill 1 from chute 4, the chute will pivot counterclockwise (arrow 67) about its supporting pivots 21 under the weight and added force of the pill mass. The pivoting action of-the chute will relieve the forces influencing the pill jam. As the jam is relieved, compression spring 15 will return chute 4 to its original position.

Agitation of the pills 1 may also be required at, and immediately around, the input 18 to tube 5. Two protruding cams 25, and two indented ridges 26 are formed about the exposed end 56 of tube 5 to provide this agitation. The agitation must be strong enough to keep large pills flowing, but gentle enough not to break or damage the pills.

The speed of the tube 5 is controlled by the rotation of the friction belt 8, which is powered by motor 7. Motor 7 is controlled by microprocessor 20 to provide the optimum speed for the type of pill or capsule being fed into the dispensing cell 100. Information about the correct speed, among other parameters, is sent to the microprocessor 20 from dispenser controller computer 509, upon the powering-up and initialization of computer 509.

Information regarding the correct speed for each individual pill type can be stored in a memory database, which database can be periodically updated as new medications are introduced into the marketplace.

A detection algorithm resides in the program of microprocessor 20. The algorithm computes the time the photocells 11 are blocked and unblocked, and also contains parameters that define the typical passage time of any specific pill 1 being currently dispensed. The algorithm makes possible the control of the dispensing system 100 by the microprocessor 20. The algorithms also provide the microprocessor 20 with information that allows the number count control of overlapping pills 1, or for the discounting of the passage of a fragment that is too small to be counted as a complete pill in the total pill count.

Funnel 10 is shaped so as to help pills and capsules maintain their longitudinal orientation for passage through the beam of photodetector 11. The funnel 10 provides for maintaining a longitudinal orientation in the pill stream exiting the collar 9. The detection algorithm will more often accurately infer the passage of one pill, two pills, or a pill fragment, when such longitudinal orientation is present in the discharge flow stream.

The cam 29 that is attached to rotating tube 5 at its inlet 18, is in contact with a micro switch 30. Cam 29 contains one large lobe, which turns micro switch 30 as it rotates past the microswitch 30 in its rotation, and then subsequently turns the microswitch 30 off. At the moment that the cam 29 turns switch 30 on, tube 5 is in a rotational position in which the final coil of the helix is far advanced. In this advanced stage, no pills 1 are remaining within the final turn of the helix. At the moment when the cam 29 turns switch 30 off, tube 5 is in a rotational position in which a group of pills 1 will be approaching the discharge point 19. The use of these switch actuations as they effect the flow of pills 1 through the dispensing cell 100, is described hereinafter, with reference to the flowchart illustrated in FIGS. 4b through 4d, describing the motor control of the dispensing cell 100 by the microprocessor 20.

Figure 2A:
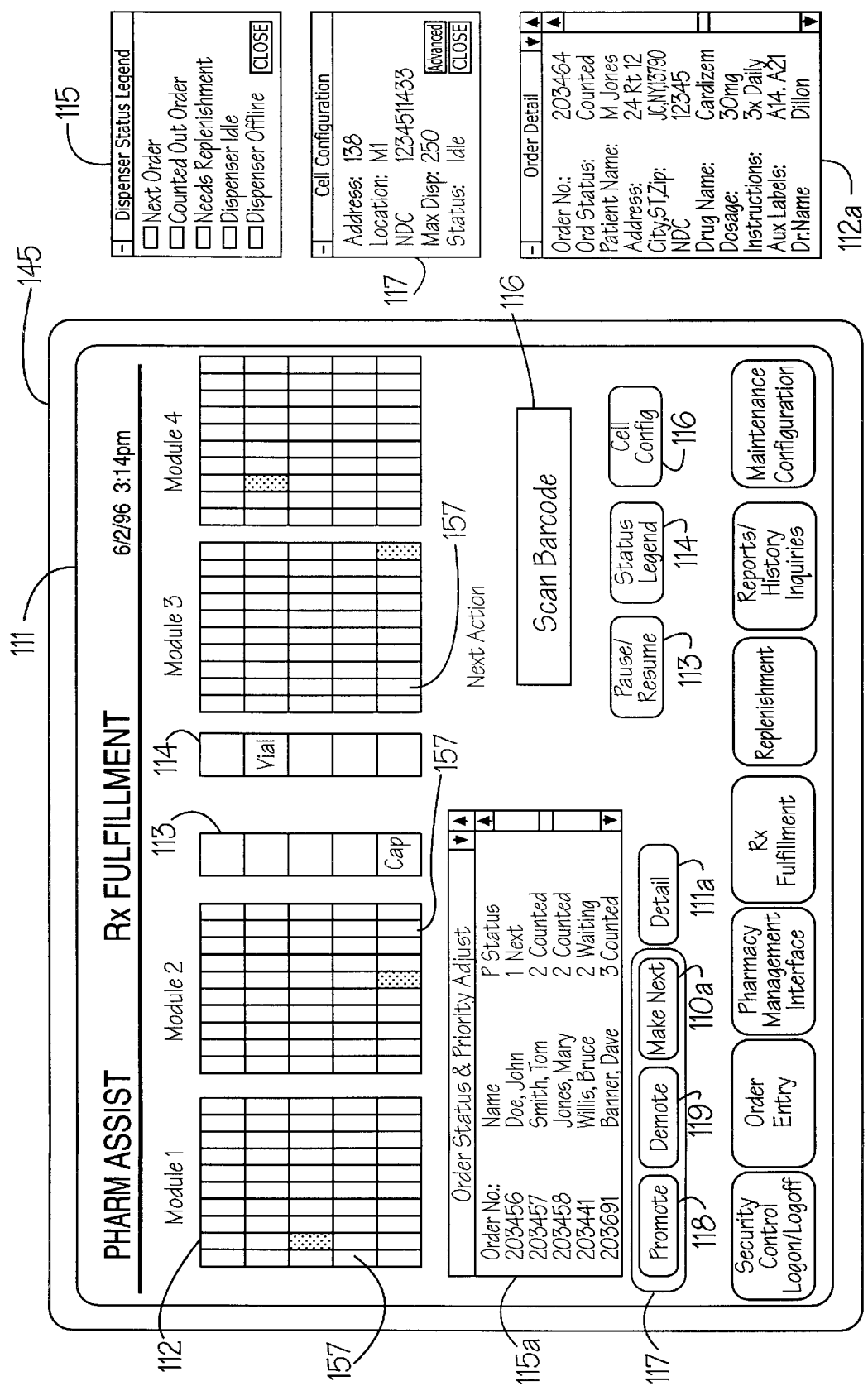
FIG. 2a shows a front view of the graphical display, including an array of modules depicted in FIG. 1b.

Referring now to FIG. 2a, video screen 145 is shown displaying a specific software-generated display 111. Shown on the display 111 are pictorial representations 112 of physical arrays or banks 510 of pill dispensing cells 100. These representations 112 illustrate individual cells 157, each corresponding to an individual, physical pill dispensing cell 100. Cells 157 assume different colors depending on the status of dispenser cell 100. For example, red indicates that dispenser 100 must be replenished; green indicates the next prescription to be released into a vial; yellow indicates an order that is already counted, but not yet released from dispenser cell 100; light gray indicates an idle dispenser; and dark gray indicates a dispenser cell 100 that is offline for maintenance, repair, or other reasons.

Other cells 113 indicate to the technician or pharmacist which size cap 154 and vial 151 to use.

Area 115 of display 111 shows the various prescription orders, the patient name, the priority with which the prescription is to be filled, and the current status of that prescription.

A pharmacist or technician can change the status of any prescription depending on whether, for instance, the customer for a particular prescription is waiting at the counter. The status is changed by the display control buttons in area 117 of display 111. If a particular prescription is selected, for example, by clicking on it with a mouse, not shown, then its priority may be made more urgent by clicking the PROMOTE button 118, or less urgent by clicking the DEMOTE button 119. The prescription can be promoted all the way to the head of the list by clicking on the MAKE NEXT button 110a.

Should the pharmacist or technician require more detail about a prescription, he or she may click on the DETAIL button 111a, at which time window 112a will appear overlaid on the display 111. Window 112a shows the detailed information for area 112.

Should the pharmacist or technician need to be reminded of the color codes for the dispenser status as shown in cells 157 of area 112, he or she can click on the STATUS LEGEND button 114, at which time the window 115a will appear overlaid on display 111.

Should the pharmacist or technician require more detail about an individual dispenser cell 100, he or she can first select the physical dispenser cell 100 by clicking on the associated cell 157, and then on the CELL CONFIG button 116. A window 117 with various information about the dispenser will appear over display 111.

Figure 2B:
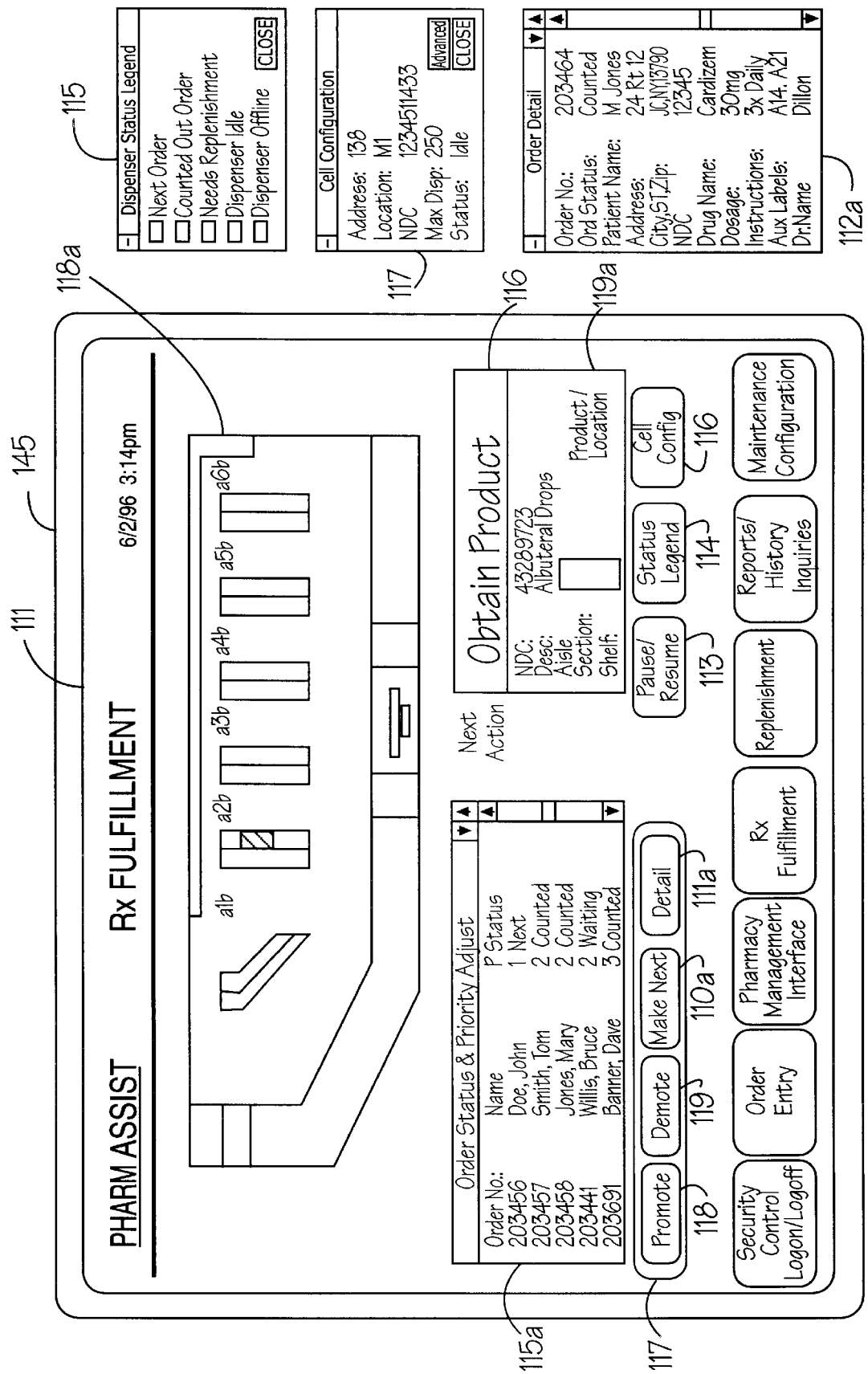
FIG. 2b illustrates a front panel view of the dispensing system depicted in FIG. 1b.

Referring now to FIG. 2b, the main computer 509 can direct a pharmacist or technician to retrieve a packaged prescription product 155 from shelves 148. To accomplish this direction, display 111 is reconfigured automatically (depending on the next prescription to be dispensed) to show the shelf layout of the pharmacy in area 118a of display 111. The shelves are numbered by aisle, section, and shelf, as illustrated. A new area 119a will appear on display 111, giving the NDC number, the name, the aisle, the section, and the shelf where the packaged product 155 can be found. Additionally, the correct spot in the layout diagram of area 118a will change color to direct the eye to the correct place.

The processes 200 and 400, respectively, depicted in the flowchart of FIGS. 3a through 3k, and the flowcharts of FIGS. 4a through 4d operate essentially in parallel and independently of each other. The process 400 of FIGS. 4a through 4d is activated once each millisecond through a timer interrupt. The two respective processes 200 and 400 communicate through the setting of modes as variables in memory. The process portion depicted in FIGS. 3g through 3k covers the action of replenishing the supply of pills, which is accomplished with the assistance of a technician and/or a pharmacist.

Dispensing cells 100 can be arrayed, as shown by the arrow 68 in FIG. 1. Each dispensing cell 100 has its own microprocessor 20. On power-up, each microprocessor 20 receives a list of control parameters from main dispenser controller computer 509. These parameters are used to control the way in which the drive motor 7 performs rapid drive rotation to move most of the pills 1 through tube 5, and slower, intermediate jogging rotation of tube 5, when the desired count has almost been reached.

In rapid counting, the motor 7 is operated at the optimum speed for the particular pill type being counted. The unit switches over to a singulation mode (intermittent jogging), when the actual pill count approaches the target pill count (e.g., within three pills of the target total pill count).

Based upon the particular size and shape of tube 5 and helix 6, the dispensing cell 100 is capable of delivering a certain population of pills with each turn of the helix. The average number of pills in this group will vary depending on the size and shape of the pills, but can be determined in advance. This information can be stored.

Based on this number, the system is able to enter into the singulation mode far enough in advance of the target count to ensure that an exact target count will be obtained. The point at which the switch to singulation mode takes place is called the singulation start point.

The parameter passed to the microprocessor 20 is the maximum group size, which is the maximum number of pills of a particular type that can be dispensed by the tube-helix combination, during any one revolution. This value is used to calculate a stored internal value, previously referred to as the singulation start count. Singulation mode is the intermittent mode in which pills are dispensed one-at-a-time from the lip 22 of the collar 9, in order to achieve the final target count. The singulation start count is that count by which the unit enters into the singulation mode. The singulation start count is calculated as follows:

[singulation start count]=[target count]−([maximum group size]−1).

The following parameters are passed to microprocessor 20 based upon pill type:

The forward pulse duration, in milliseconds, is the duration of the main pulse that drives the next pill from the collar lip 22.

The forward pulse pause, in milliseconds, is the duration of the pause between pulses.

The pill drop reverse time, in milliseconds, is the amount of time the helix will be driven in reverse after each detected pill, to allow the group of pills to settle back down into the center of the collar.

The jog count is used for particularly difficult pills where an additional jogging motion is required. The jog count specifies a certain number of forward pulses, after which the helix is reversed a certain amount to let the pills settle.

The jog reverse time, in milliseconds, specifies the duration of the reversal after the specified number of forward pulses has occurred.

The microprocessor 20 senses the signal produced by photodetector 11 and computes the durations of pulses produced as pills fall through. Microprocessor 20 is sent the following information:

The minimum pill width, in milliseconds, is the shortest amount of time this particular type has taken to pass through the photodetector beam. Once established, any shorter pulses may be considered to be pill fragments and discarded in the final count.

The maximum pill width, in milliseconds, is the longest amount of time this particular type takes to pass through the photodetector beam. Once established, the microprocessor can distinguish doubles, because any pulses of longer duration can be considered to be two pill s falling through the beam, despite the fact that the photodetector will provide a single pulse due to the closeness of the pills as they pass the sensors.

Pill-to-pill separation, in milliseconds, is the shortest time in milliseconds between two successive pills of this type as they pass through the detector. Pills may safely be considered to be separate pills, if two pills are in fact separated by more than this time.

The flowcharts, described in greater detail hereinbelow, illustrate that when counting is complete, the microprocessor 20 will inform dispenser controller computer 509 of this fact. Dispenser controller computer 509 will then execute a protocol to inform a technician or pharmacist of the next prescription to fill. Thereafter, when it is time for this particular dispenser to dispense pills, computer 509 informs microprocessor 20, which turns on the indicator light on the dispenser. Computer 509 also prints a label 150 and requests the technician or pharmacist to place it on a vial 151 and to wand the barcode on the label 150. After checking that the barcode represents the correct prescription, computer 509 asks the technician or pharmacist to fill the vial 151 from the dispenser cell 100. The placement of the vial 151 under the dispenser cell 100 by the technician or pharmacist activates microswitch 50. The microprocessor 20 then actuates solenoid 14 to open door 13 and dispense the pills into the vial 151. The switch 50 informs the microprocessor 20 whether door 13 is open or closed.

Figure 5:
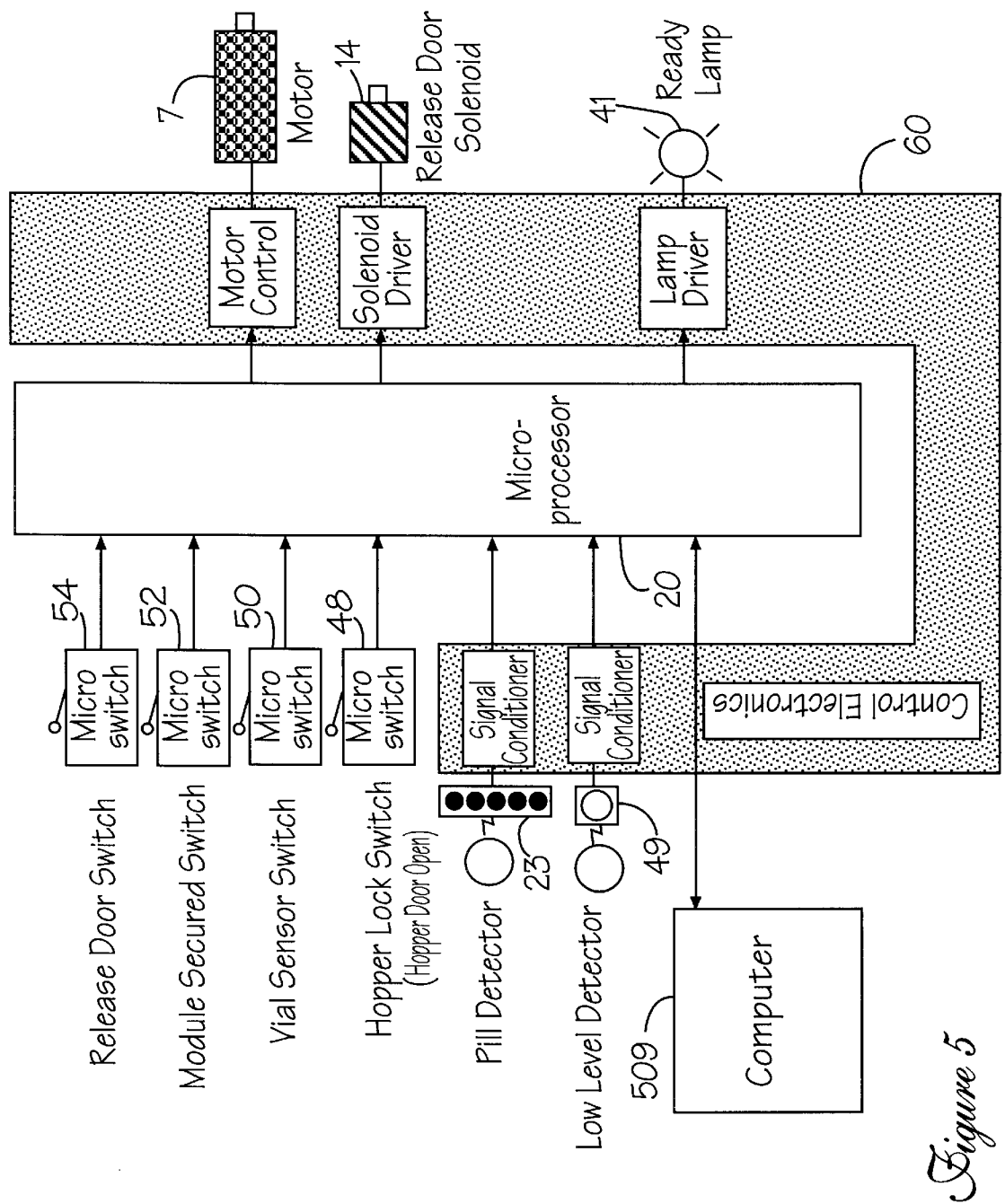
FIG. 5 illustrates a schematic, diagrammatic view of the electronic, computerized circuit of the pill dispensing system depicted in FIG. 1.

Referring to FIG. 5, the electronic, computerized circuit of each pill dispensing cell 100 is illustrated. The electronics 60 contains a number of sensor amplifiers and drive amplifiers that service the respective components of the system, such as: motor 7, release door solenoid 14, ready lamp 41, pill detecting apparatus 23 and 24, and pill low level detecting apparatus 49 for hopper 2. Release door switch-54, module secured switch 52, vial sensor switch 50, hopper door switch 48, pill detector 23, pill low level detector 49, motor 7, release door solenoid 14, and ready lamp 41 are shown in FIG. 1, and are described in greater detail with reference to the following explanation of the flowcharts.

As aforementioned, the processes 200 and 400, respectively, depicted in the flowchart of FIGS. 3a through 3k, and the flowcharts of FIGS. 4a through 4d operate essentially in parallel and independently of each other. The processes 300 and 400 of FIG. 4a and 4b through 4d, respectively, are activated once each millisecond-through a timer interrupt. The respective process 200 and processes 300 and 400 communicate through the setting of modes as variables in memory. The process portion depicted in FIGS. 3g through 3k covers the action of replenishing the supply of pills, which is accomplished with the assistance of the replenishment technician 512.

Now referring to FIGS. 3a through 3k, the dispensing routines process 200, is illustrated. After the powering and initialization of the microprocessor 20 and the controller computer 509, the rapid-counting speed is communicated to the microprocessor 20 from the controller computer 509, step 201. The rapid-speed information is specific to the type of pill being dispensed. This information is necessary in order to rotate the combination of the tube 5 and the helix 6 at the most efficient speed. The maximum group size for this pill type is also communicated from the dispenser-controller computer 509, step 202. Other information for this particular type of pill is communicated to the microprocessor, including: the forward pulse duration, step 203, the forward-pulse pause duration, step 204, the pill-drop reverse duration, step 205, the jog count,,step 206, the jog-reverse time, step 207, the minimum and maximum pill widths, steps 208 and 209, respectively, the maximum number of this type of pill to be dispensed, step 210, the pattern for operating the release door 13 in order to shake clogged pills loose, step 211, and the pill-to-pill separation information, step 212. The computer routine then inquires whether this information has been received, step 213. The system then inquires as to how many pills remain in the hopper 2, step 214, and how many pills remain in the dispensing chute 12, step 215.

Figure 3A:
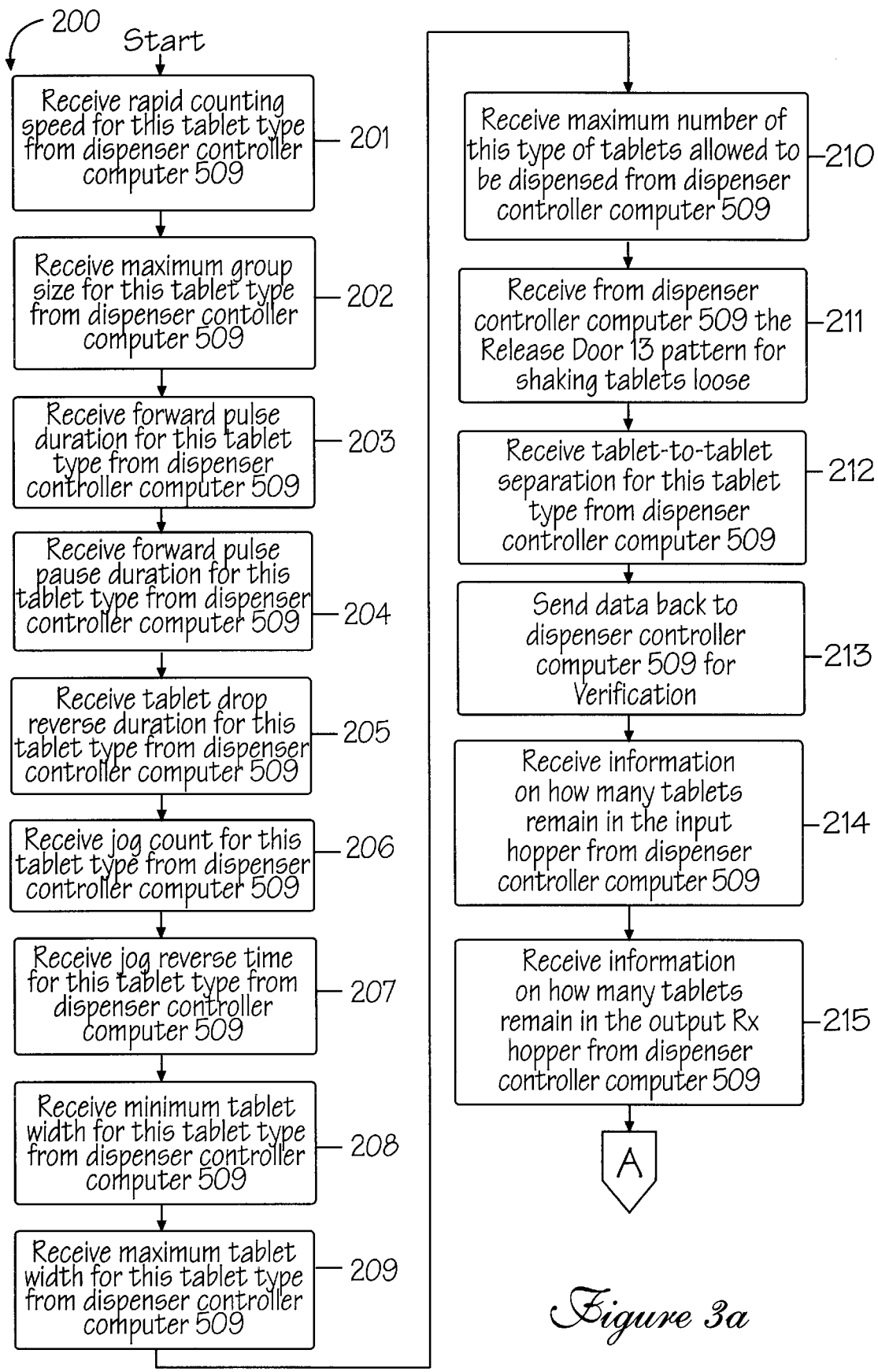
FIGS. 3a through 3e show a flowchart of the operation of the pill dispensing system, illustrated in FIG. 1.
Figure 3B:
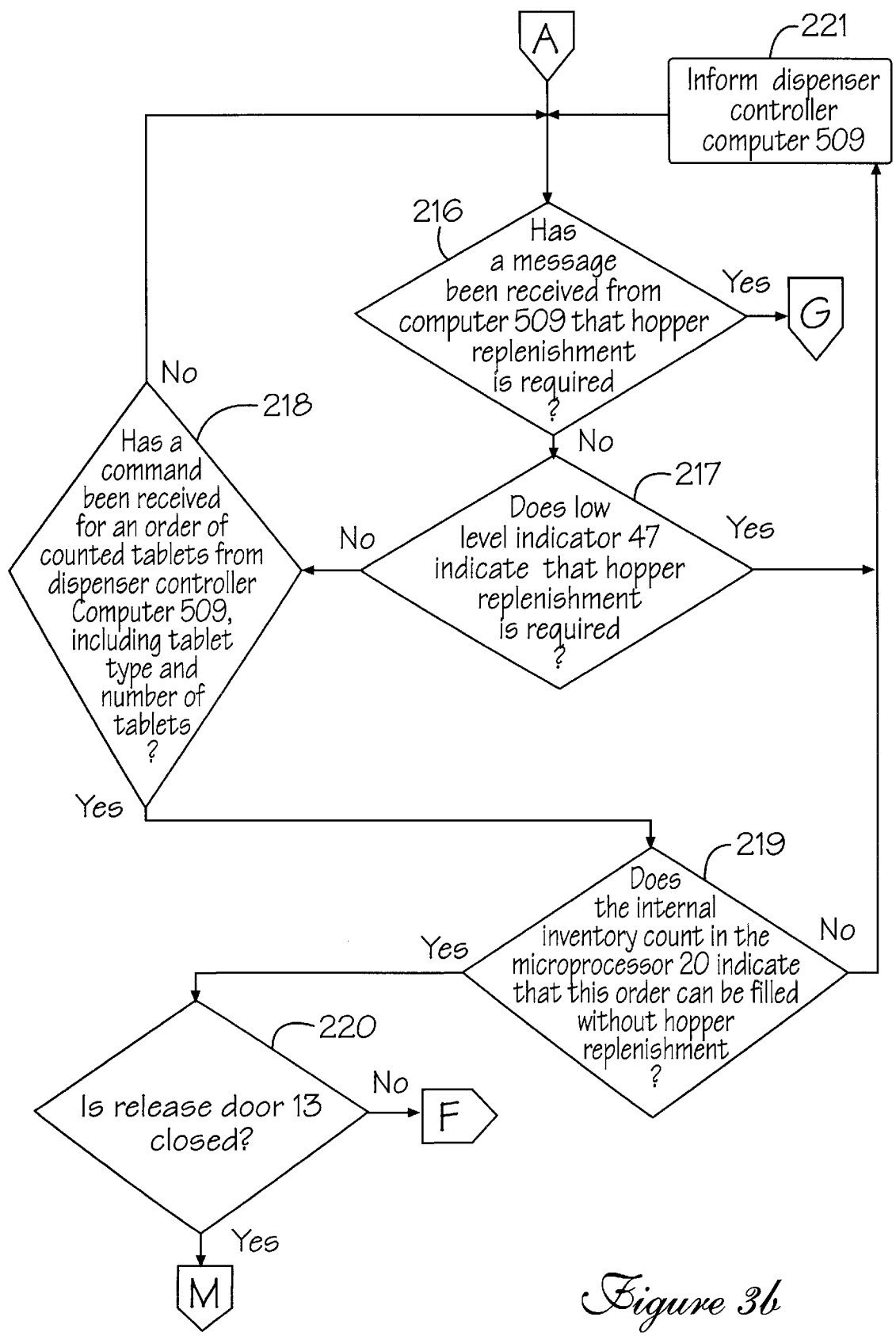

Decision step 216 is then entered (FIG. 3b). When the question of whether hopper replenishment is required is answered with a "no", decision step 217 is then entered. If hopper replenishment is required, step 216, then the system is so informed.

If the low-level indication does not suggest replenishment, step 217, then the system determines whether an order for pills has been received from the computer 509, step 218. If not, then decision step 216 is re-entered. If yes, then the system asks whether there are enough pills in the inventory, so that the order can be filled without replenishment being necessary, step 219. If the answer is no, then the computer 509 is informed, step 221, and decision step 216 is re-entered. If yes, step 219, then the system asks whether the release door 13 is closed, step 220. If not, then the system reports faulty operation to the computer 509, step 223 (FIG. 3e). The pharmacist or technician is then instructed to await further instructions, step 224.

Figure 3C:
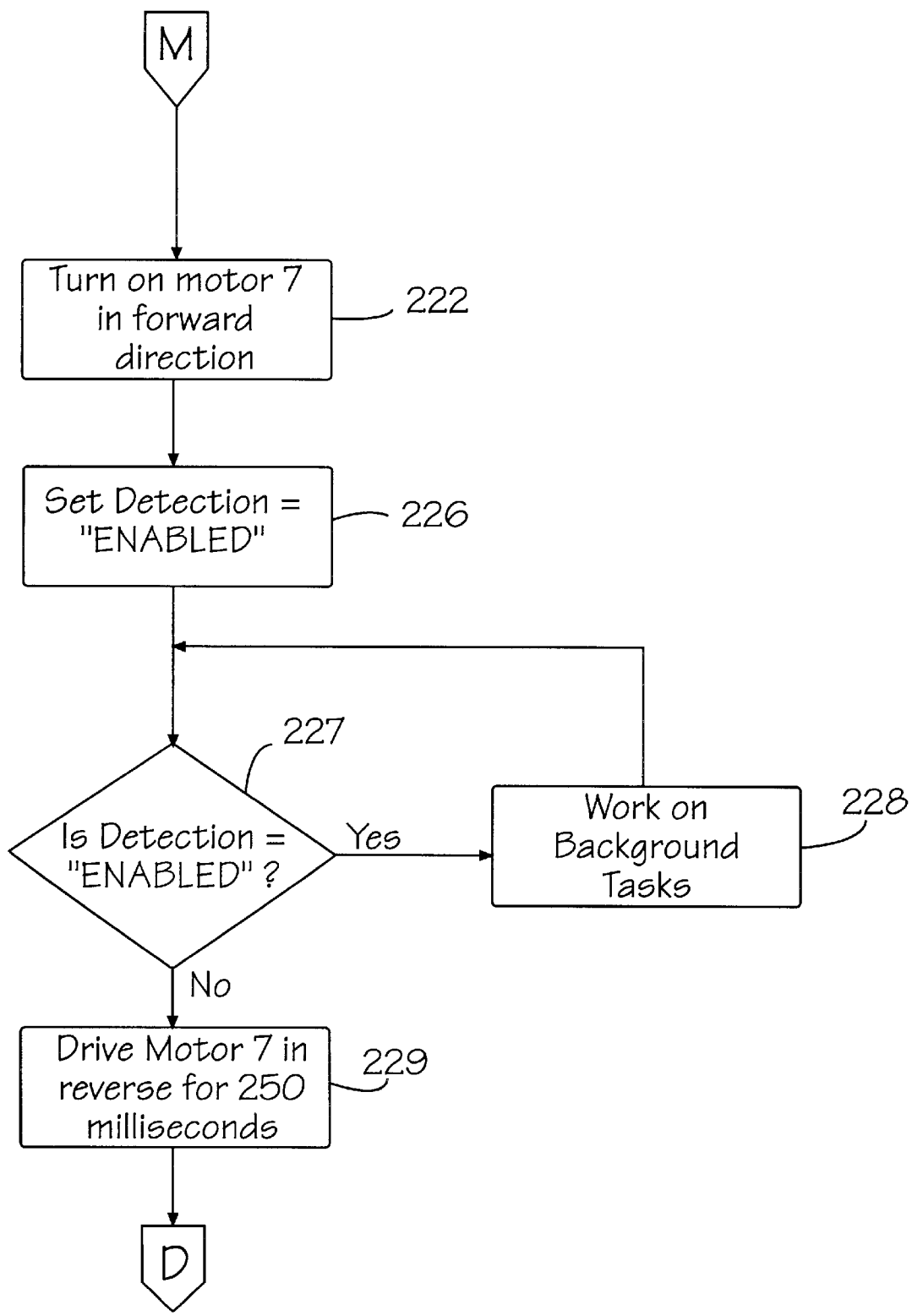

If the release door is closed, step 220, the motor 7 is turned on in the forward direction, step 222 (FIG. 3c). The set detection="ENABLED" signal is given, step 226, and then the system inquires as to whether the detection signal has been set enabled, step 227. If so, microprocessor 20 is freed to work on background tasks, step 228, and decision step 227 is re-entered. If the answer to the detection question, step 227, is no, then drive motor 7 is reversed for a predetermined period of time, typically 250 milliseconds, step 229.

Figure 3D:
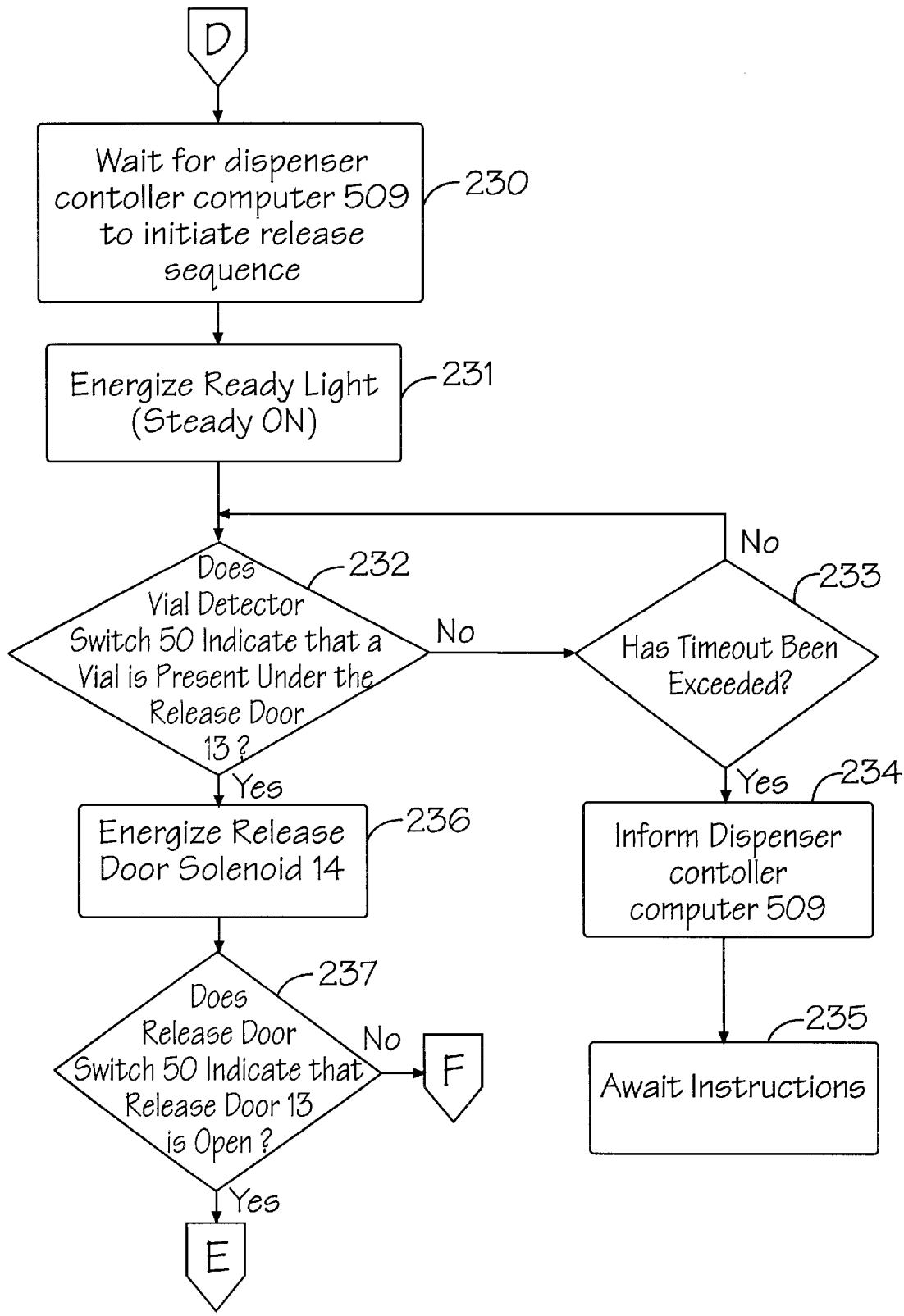
Figure 3E:
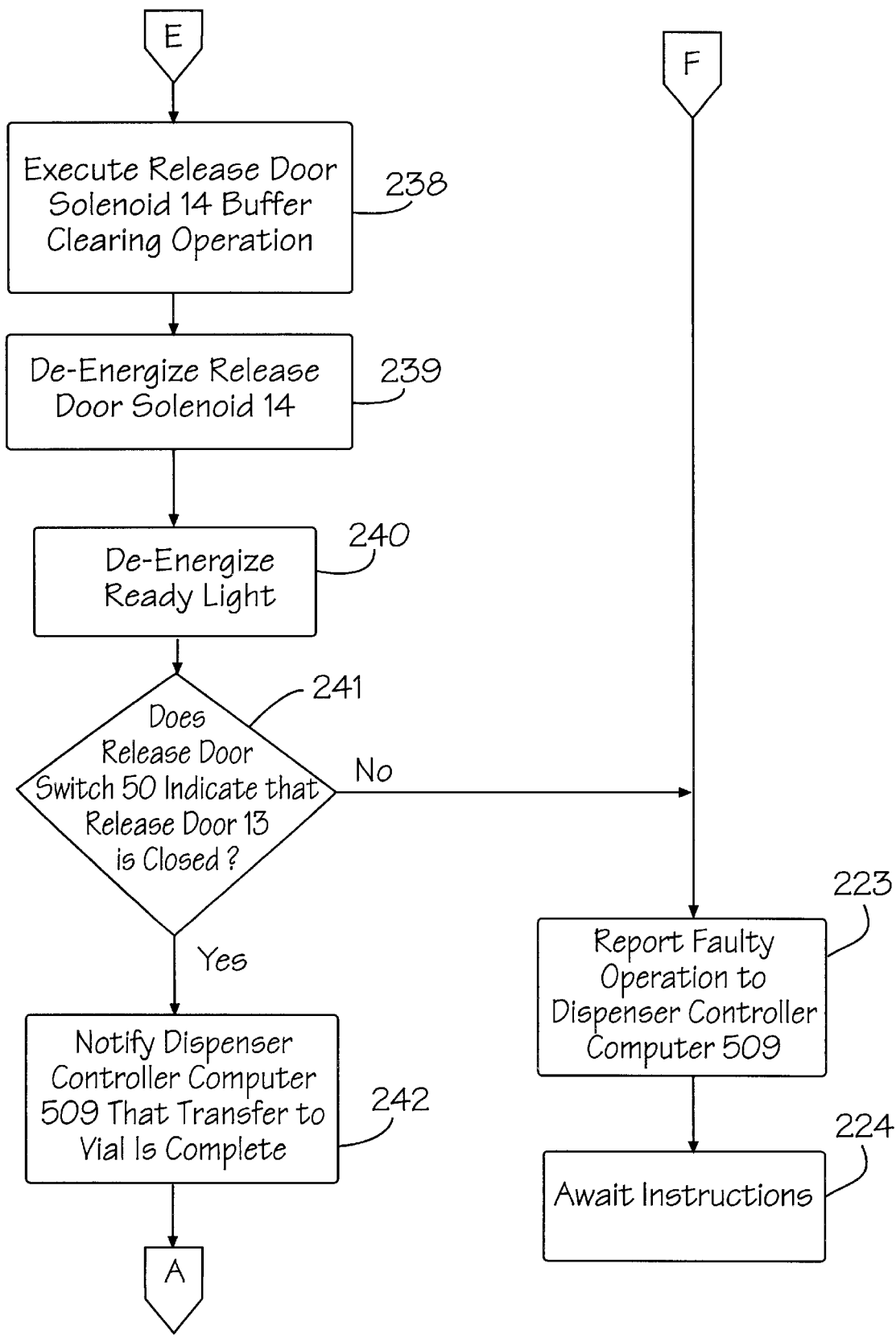

After computer 509 has issued a release command, the release sequence is initiated, step 230 (FIG. 3d). The ready light is then energized, step 231. The routine then asks whether a vial is present under the release door 13, step 232. If not, the system determines whether a predetermined time-out has been exceeded, step 233. The computer 509 is then informed of the time-out and microprocessor 20 awaits further instructions, steps 234 and 235. If the time-out has not been exceeded, step 233, the system re-executes step 232. If a vial is present under the door 13, step 232, then the door release is energized, step 236. If the release-door switch 50 indicates that there has been no release, then the steps 223 and 224 (FIG. 3e) are performed, as previously described.

If, however, the release-door switch 50 indicates that a release occurred, step 237, the system releases the solenoid 14, and clears the buffer, step 238 (FIG. 3e), whereupon the solenoid 14 is de-energized, step 239. The system de-energizes the ready light, step 240, after which the system inquires as to whether the indicator switch 50 shows that the release door 13 is closed, step 241. If not, then steps-223 and 224 are performed, as before. If the release door is closed, step 241, then computer 509 is informed that the transfer to the vial has been completed, step 242. Having accomplished this, the routine re-enters decision step 216 (FIG. 3b).

Figure 3F:
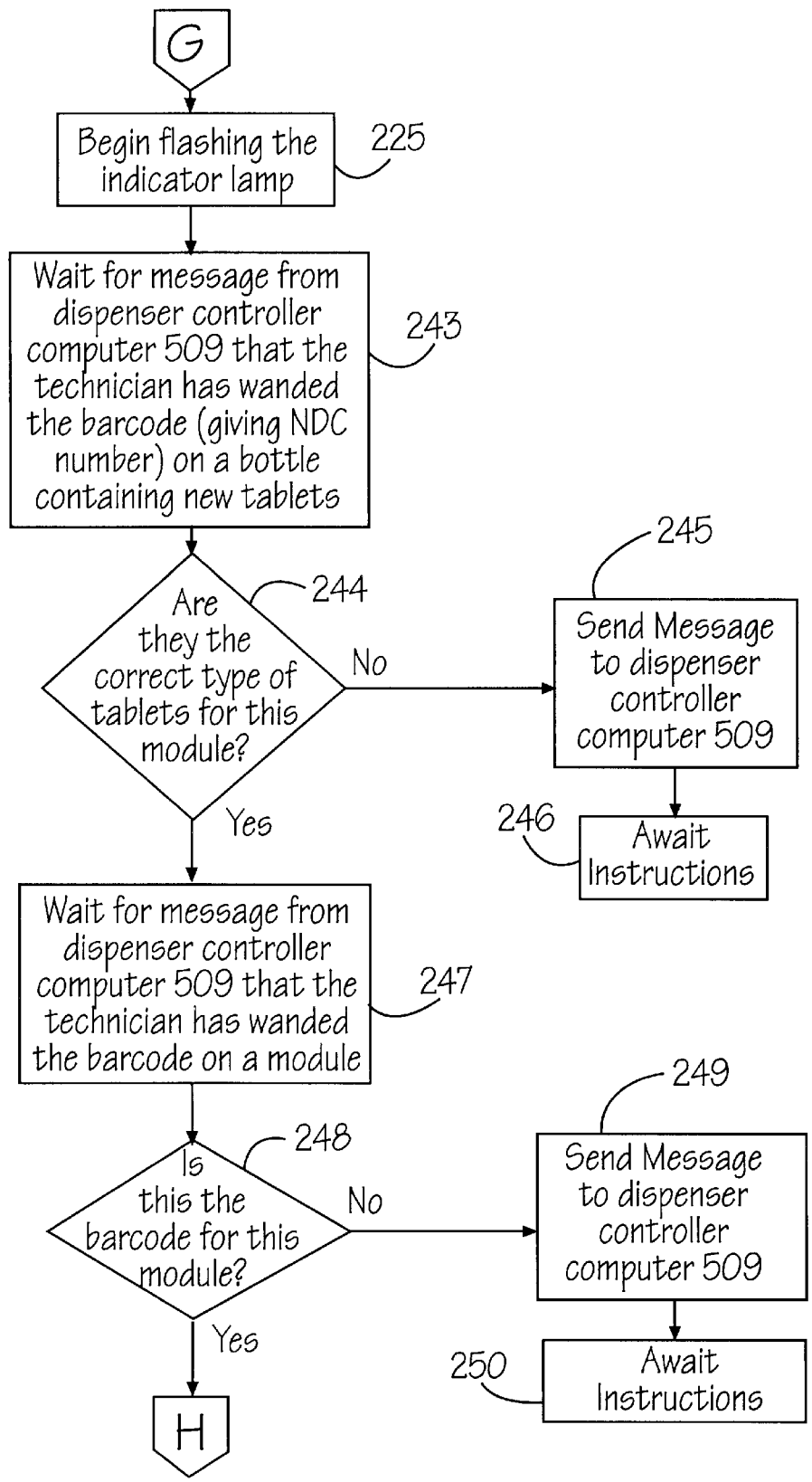
FIGS. 3f through 3k illustrate a flowchart of the replacement procedure used in the pill dispensing system depicted in FIG. 1.
Figure 3G:
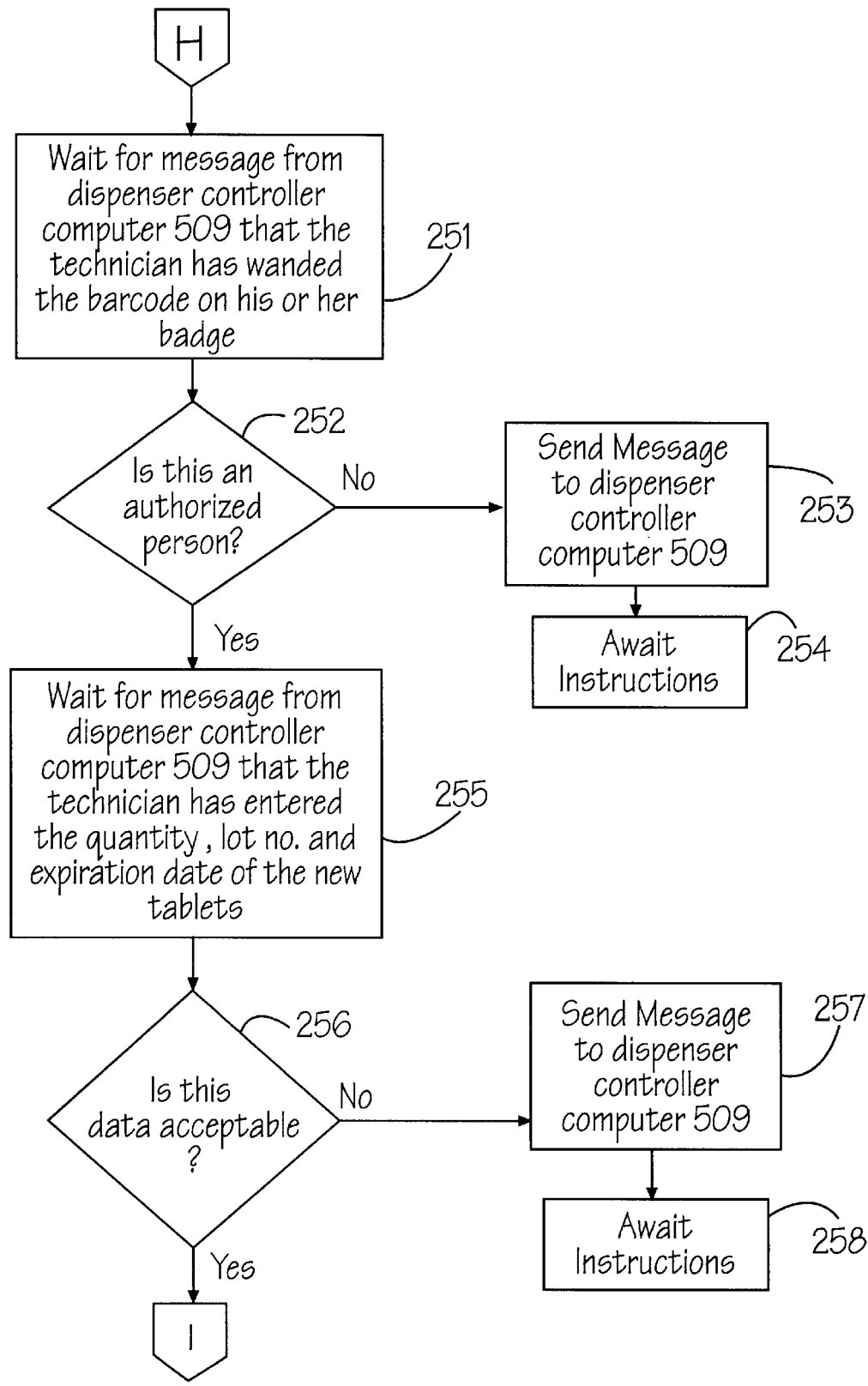

Hopper replenishment is indicated by the flashing indicator lamp, step 225 (FIG. 3f). The system then waits for the wanding of the barcode signal from computer 509, step 243. The system determines whether the actual pills are the type specified for the module, step 244. If not, then the system informs the computer 509, step 245. A message is given, step 246, to wait for further instructions.

Should the type of pills dispensed be correct, then the system is asked to wait for a message that the barcode has been wanded, step 247; The system then determines whether this is the correct barcode, step 248. If not, then a message is sent to computer 509, step 249, and the system awaits further instructions, step 250. If the barcode is correct, step 248, then the system is instructed to wait for a message from the computer 509 that the technician 514 has wanded the barcode with his or her authentication badge, step 251.

The system then determines whether the operator is authorized, step 252. If not, then the computer 509 is notified, step 253, and the system awaits further instructions, step 254. If yes, then the system waits for the message that the replenishment technician 512 has entered the proper data on the vial label, step 255. The system then determines whether the data is acceptable, step 256. If not, then the computer 509 is notified, step 257, and the system awaits further instructions, step 258.

Figure 3H:
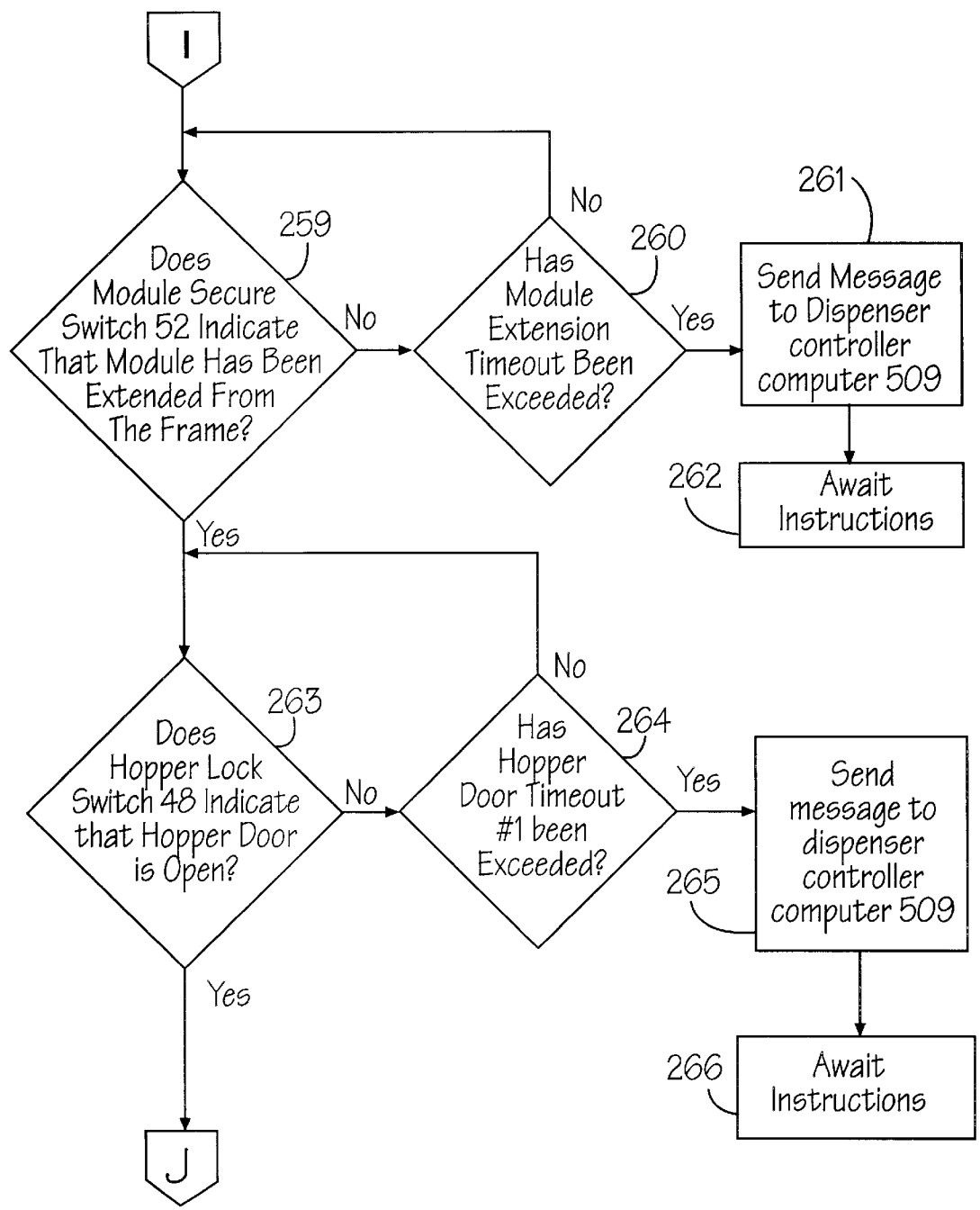

If the data is acceptable, step 256, then the system determines whether the secure switch 52 (FIG. 1) indicates that the module has been extended from its frame, step 259 (FIG. 3h). If not, then the system determines whether the module extension time out has been exceeded, step 260. If not, then decision block 259 is re-entered. If the time has been exceeded, step 260, then this message is sent to computer 509, step 261, and the system awaits further instructions, step 262. If the module has been extended from its frame, step 259, then-the system determines whether the hopper lock switch 48 (FIG. 1) is open, step 263. If switch 48 is not open, then the system determines whether the door time out has been exceeded, step 264, and, if not, loops through step 263 again. If time has expired, however, step 264, then the message is sent to computer 509, step 265, and the system awaits further instructions, step 266.

Figure 3I:
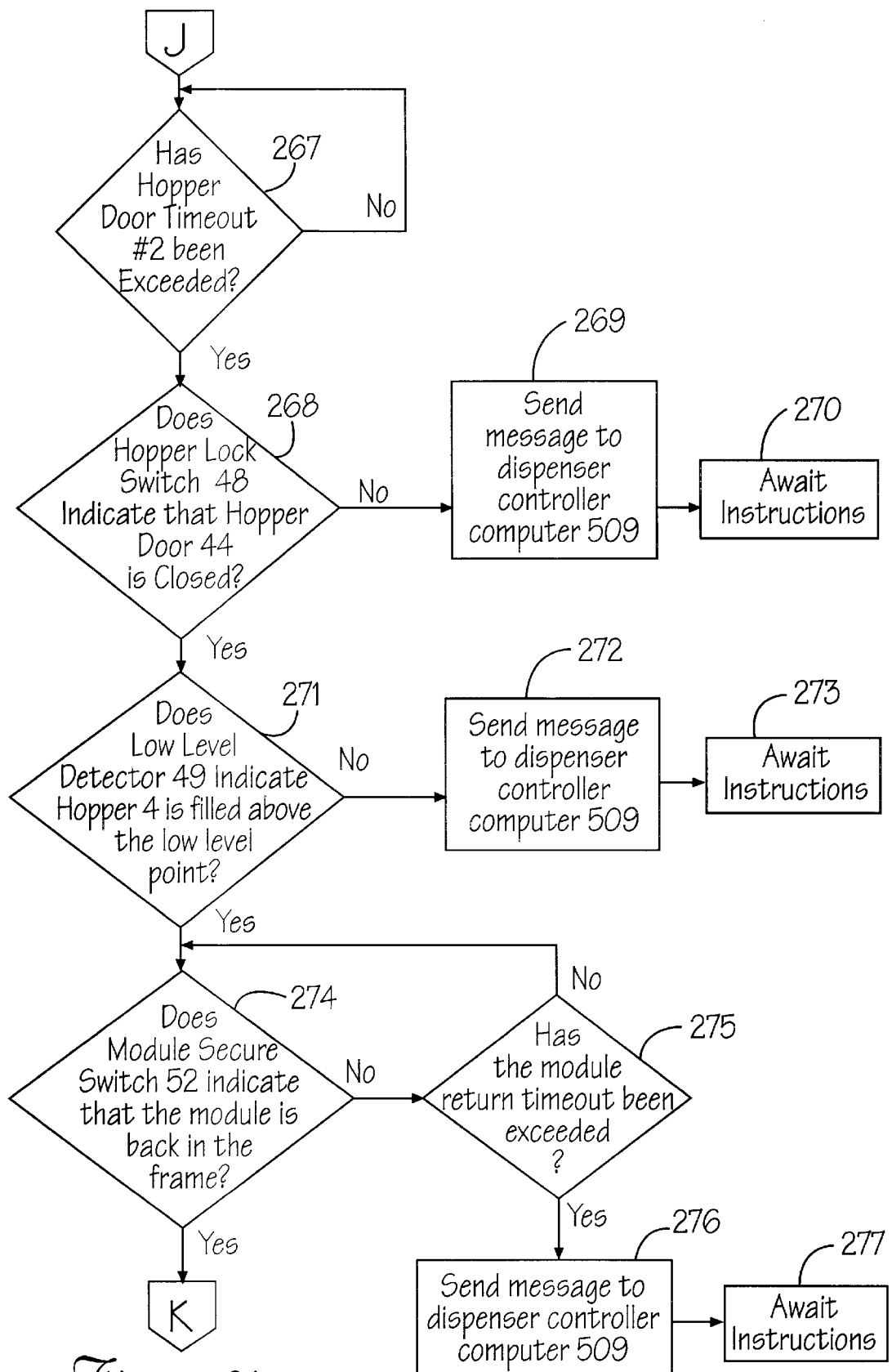

If the indication is that the hopper door is open, step 263, then the system determines whether a second predetermined time period has been exceeded, step 267 (FIG. 3i). If not, then the routine loops or waits until an affirmative answer is received. The system determines, step 268, whether the hopper door lock switch 48 is on, indicating that the hopper door 44 is closed. If not, then the computer 509 is sent an appropriate message, step 269, and a request is generated by the system to await further instructions, step 270. If the answer to the question of whether hopper door 44 is open is yes, step 268, then the system determines whether the low level detector 49 indicates that the hopper is filled to above the low level mark, step 271. If not, the message is sent to computer 509, step 272, and a request is made to await further instructions, step 273.

If the indication is that the level in the hopper is above the low level mark, step 271, then the system determines whether the secure switch 52 indicates that the module is back in its frame, step 274. If not, the system determines whether the module return timeout has been exceeded, step 275, looping through step 274 until the timeout is expired, step 275. When the timeout expires, step 275, a message is sent to computer 509, step 276, and the system-awaits further instructions, step 277.

Figure 3J:
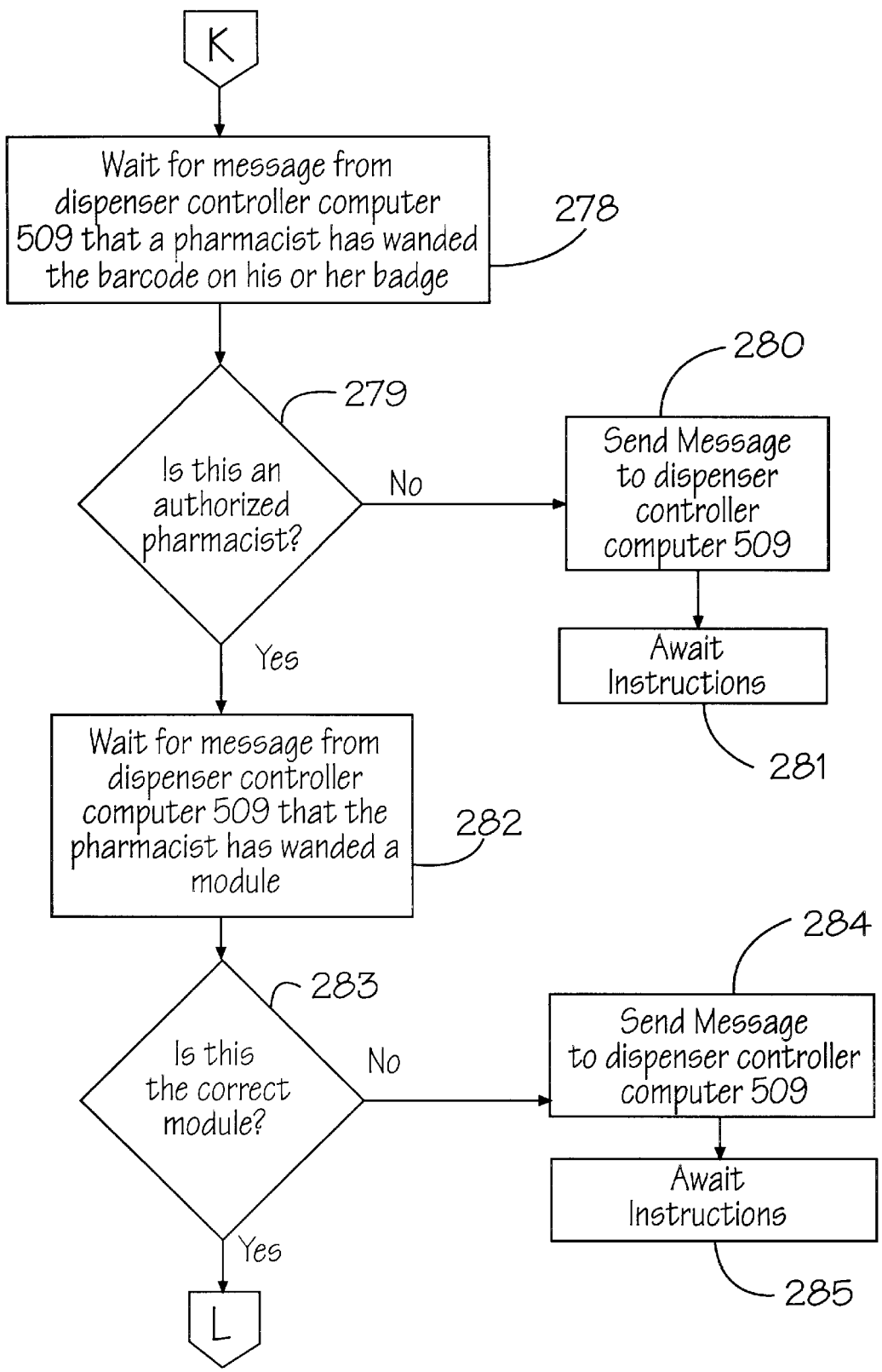

If the module is back in the frame, step 274, however, then the system is instructed to await for the wanding of the barcode on the badge of the pharmacist, step 278 (FIG. 3j). The system determines whether the pharmacist/technician is authorized to work in the system, step 279. If the technician is not authorized, step 279, the system informs computer 509, step 280, and awaits further instructions, step 281. If the authenticity is proper, step 279, then the system waits for the wanding by the pharmacist of the module, step 282.

The system then determines whether this is the correct module, step 283. If not, then an appropriate message is displayed, step 284, and the system awaits further instructions, step 285.

Figure 3K:
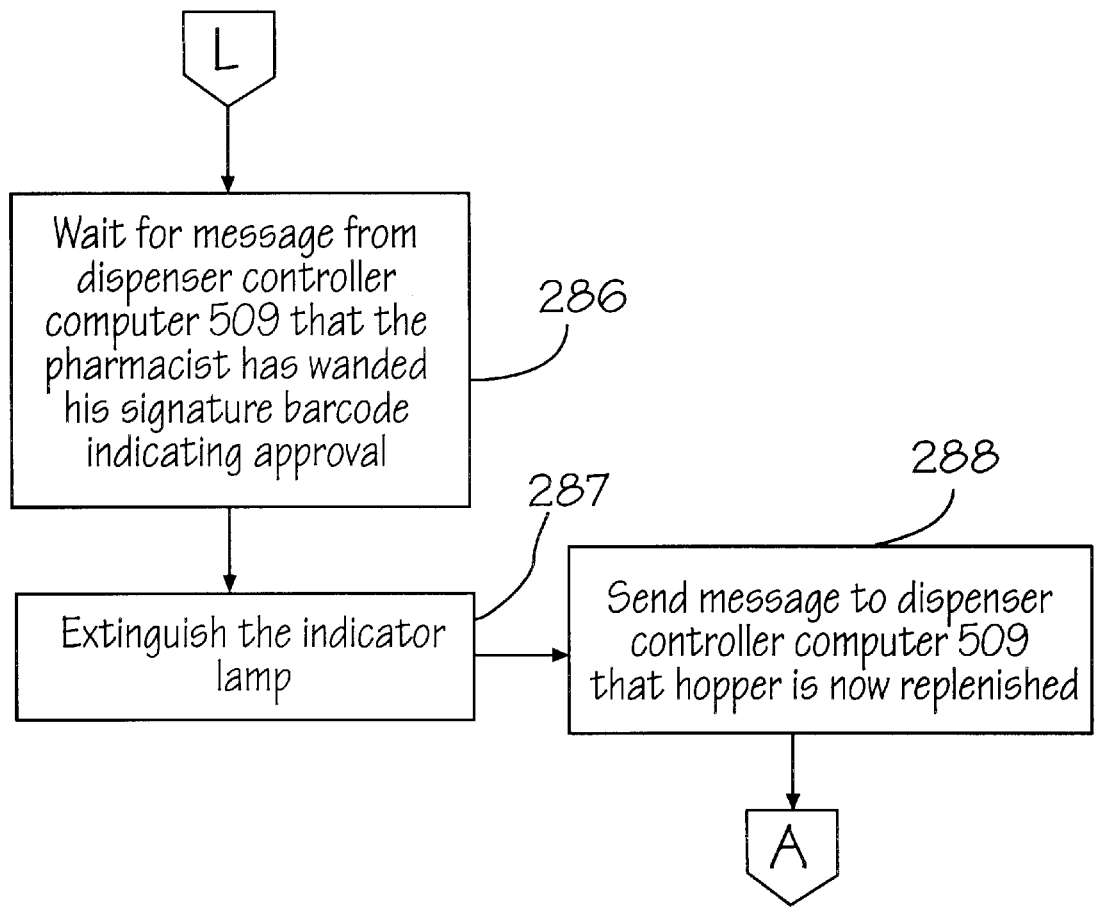

If the correct module has been accessed, step 283, then the system is instructed to wait for a message from computer 509 that the pharmacist has wanded his signature barcode, indicating approval, step 286 (FIG. 3k). The indicator lamp is then extinguished, step 287. A message that the hopper is now replenished is sent to computer 509, step 288. The process of replenishment is repeated, step 216 (FIG. 3b), as it becomes necessary.

Figure 4A:
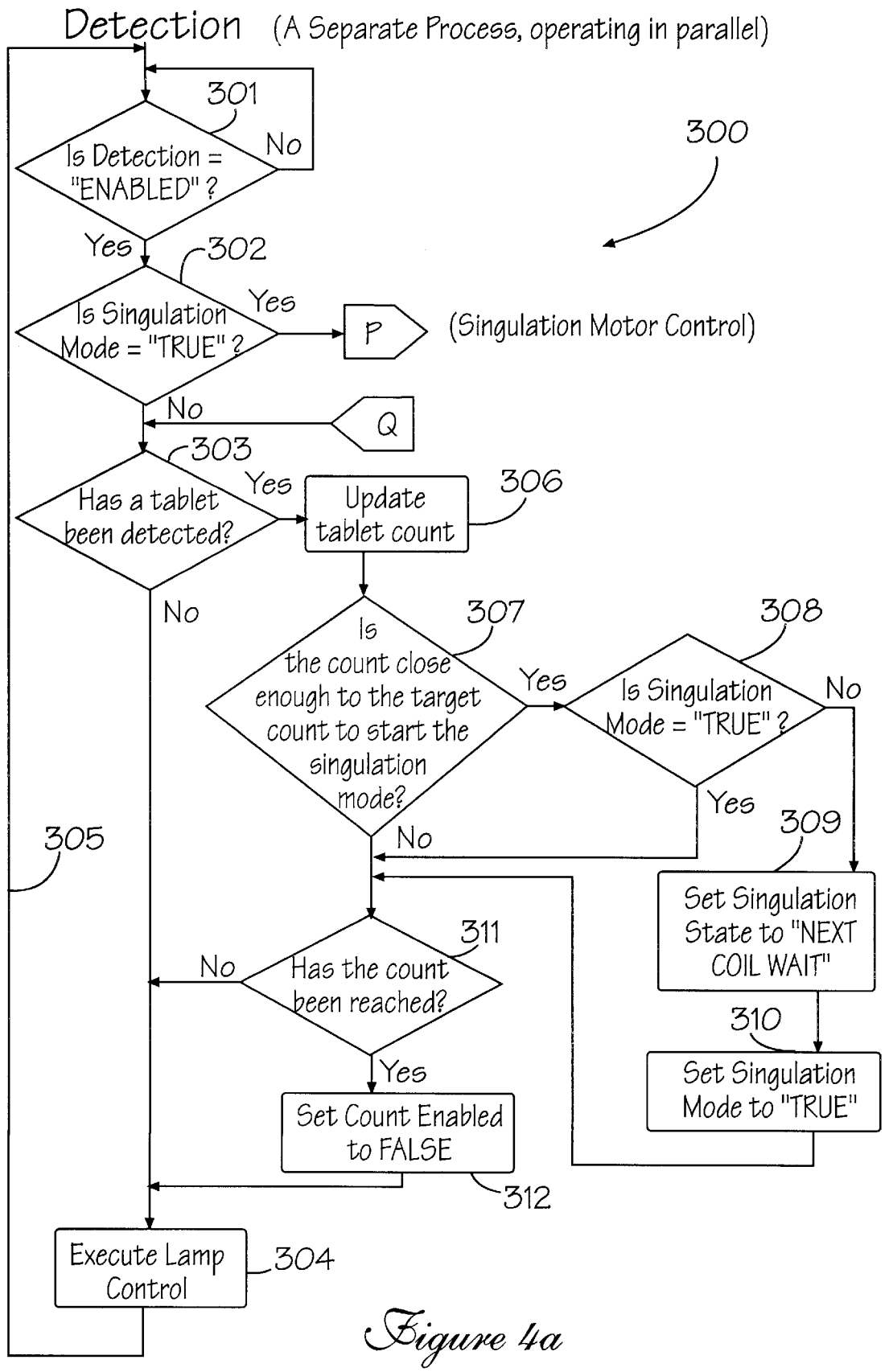
FIG. 4a depicts a flowchart for the detection of the pills being dispensed from the dispensing system shown in FIG. 1.
Figure 4B:
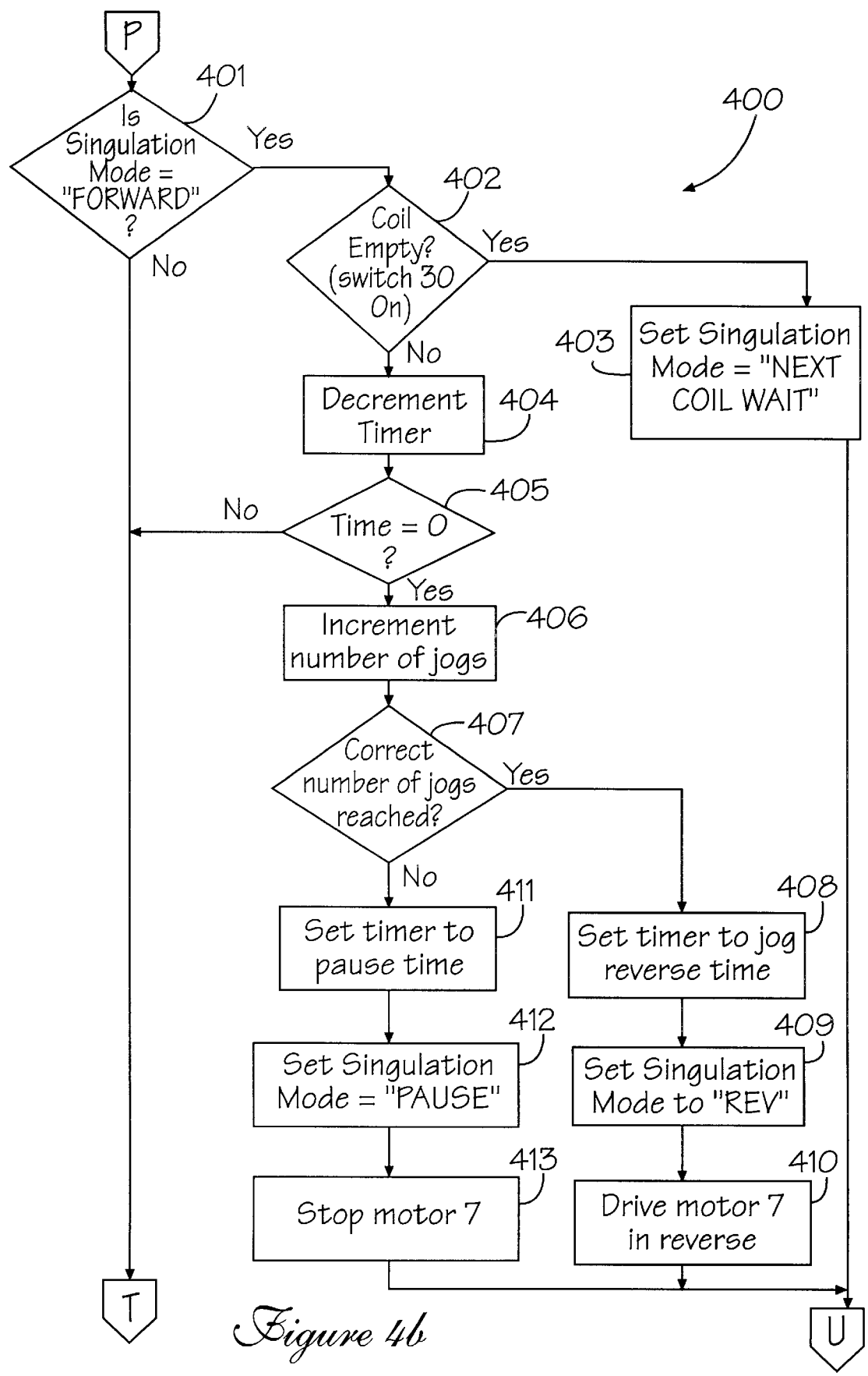
FIGS. 4b through 4d show a flowchart of the singulation motor control for the pill dispensing system illustrated in FIG. 1.
Figure 4C:
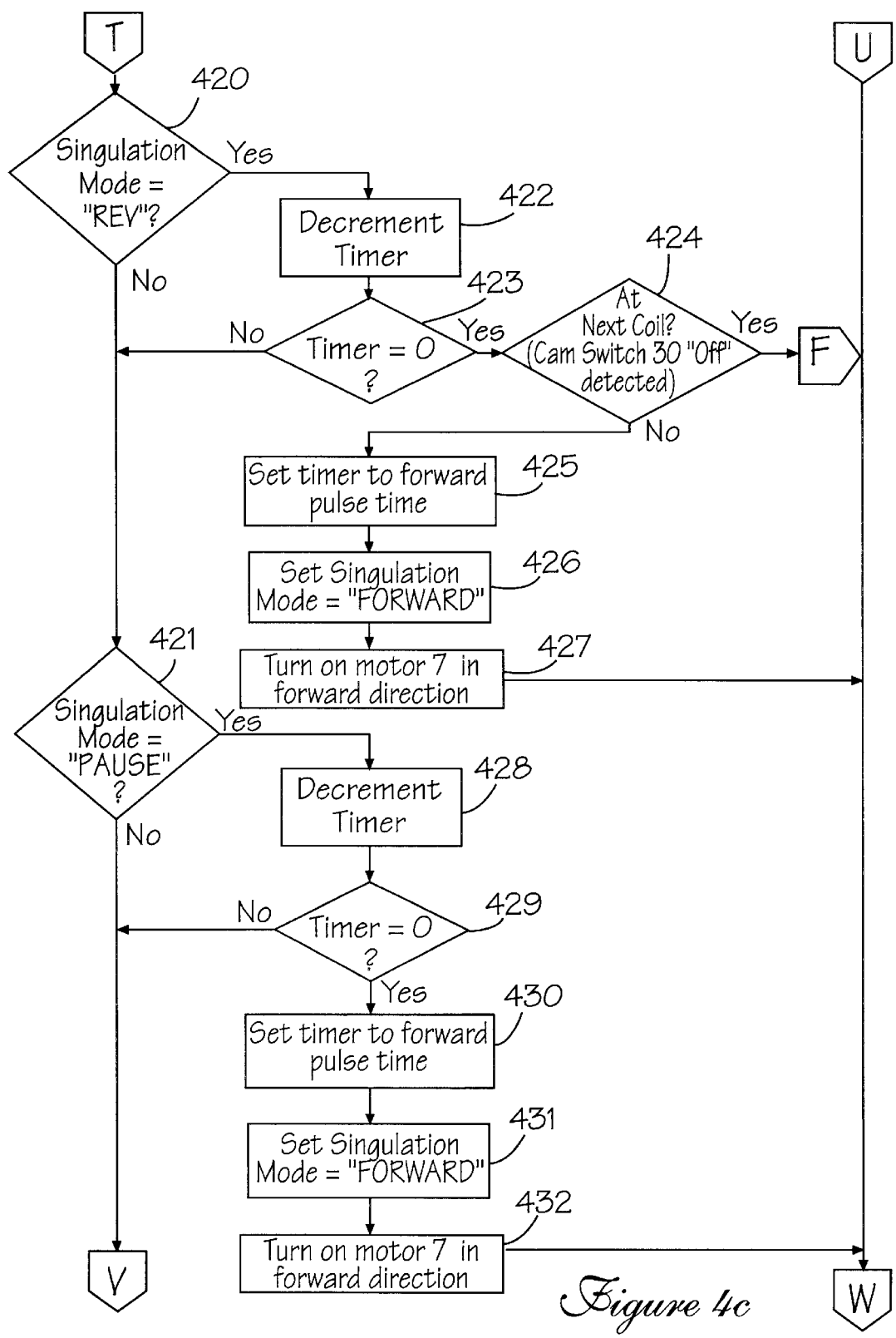

Now referring to FIG. 4a, the process 300 of detection is illustrated. After powering and initializing the computer and the microprocessor, the detection program is operative. The system determines if detection is enabled, step 301. If not, the system waits until it is determined that detection is enabled, step 301. If the singulation mode is on, step 302, the routine jumps to the singulation motor-control routine 400 (FIG. 4b). If the singulation mode is not "TRUE", then the system determines whether a pill has been detected, step 303. If not, the lamp control is executed, step 304, and decision step 301 is re-entered via line 305. If a pill has been detected, step 303, then the pill count is incremented based on output from the detection algorithm, step 306. The system then determines whether the count is close enough to the target count to begin singujation mode, step 307. If so, the system determines whether singulation mode is still "TRUE", step 308. If the count is sufficiently close, step 307, but the singulation mode has not been entered, step 308, then the singulation state is set to "NEXT COIL WAIT", step 309, and the singulation mode is set to "TRUE", step 310.

It is then decided whether the count has been reached, step 311. If not, the lamp control is executed, step 304, and-the decision step.301 is re-entered, via line 305. If the count has been reached, step 311, the count enabled is set to "FALSE", step 312, before lamp control is executed, step 304. The decision step 301 is then re-entered, via line 305.

Referring to FIG. 4b, the singulation motor-control process 400 and decision step 401 are entered, as aforementioned, from decision step 302 of FIG. 4a. If the system determines that singulation mode is not running forward, step 401, then the routine jumps to the decision step 420 of FIG. 4c, described below. If yes, however, the system determines whether the switch 30 is on, step 402. Switch 30 indicates a jam at the inlet 18 of the tube 5. If the answer is yes, the singulation mode is set to "NEXT COIL WAIT" state, step 403. The routine then jumps to the detection process 300 of FIG. 4a, and enters the decision step 303. If the answer is no (switch 30 is off), step 402, then the timer is decremented, step 404. If the time has not reached zero, however, step 405, then the routine jumps to decision step 420 of FIG. 4c. If the time has reached zero, however, step 405, the number of jogs of the tube 5 is incremented, step 406. The system determines whether the correct number of jogs has been reached, step 407. If yes, the timer to jog-reverse time is set, step 408, the singulation mode is set to "REVERSE", step 409, and the drive motor 7 is reversed, step 410.

The routine then reverts to decision step 303 of the detection program (FIG. 4a). If the correct number of jogs has not been reached, step 407, then the timer is set to pause-time, step 411, the singulation mode is-set to "PAUSE", step 412, and motor 7 is stopped, step 413. The routine then jumps to decision step 303 (FIG. 4a).

Figure 4D:
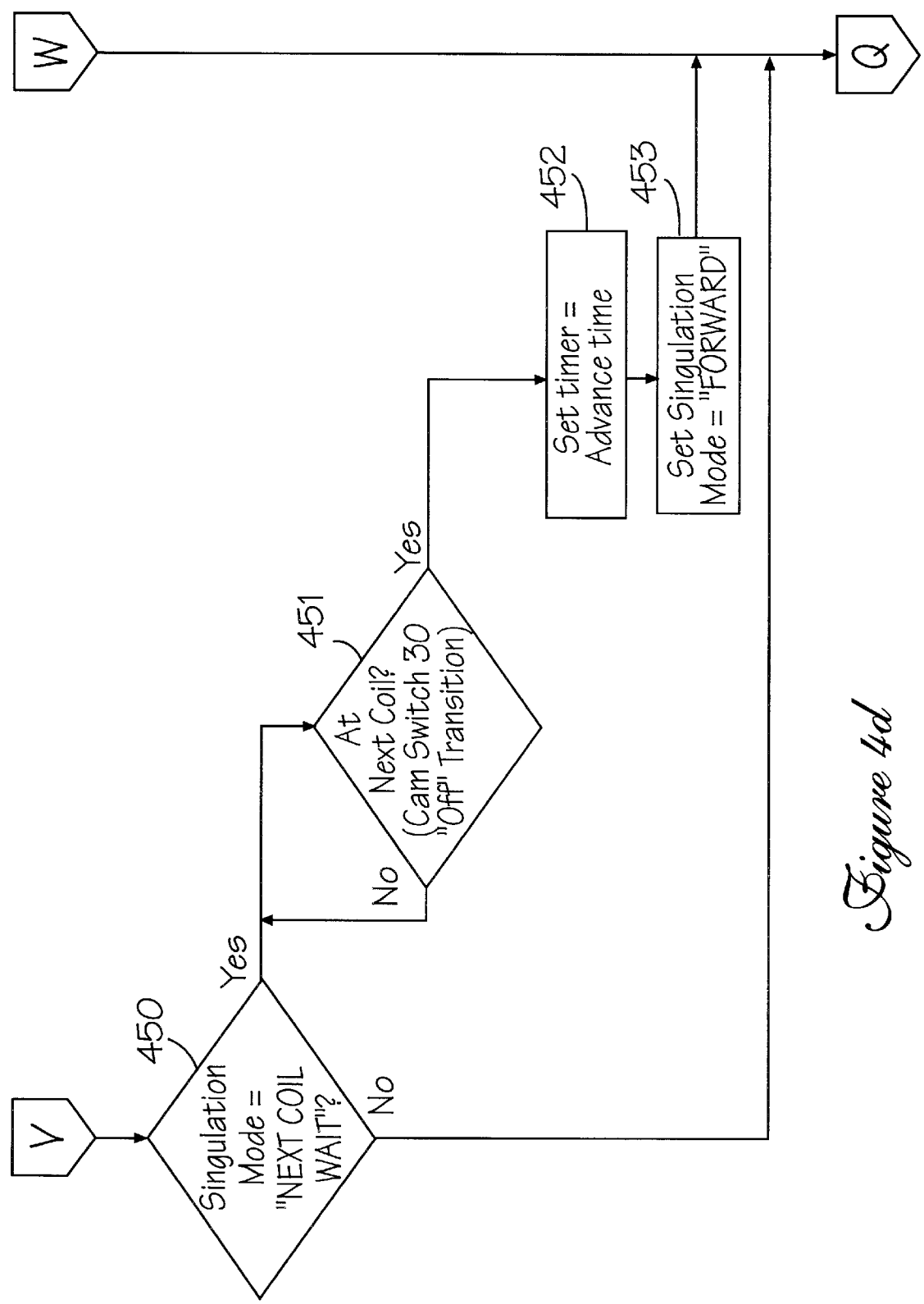

In jumping to decision step 420 (FIG. 4c) from either step 401 or step 405, the program determines whether the singulation mode is in the "REVERSE" state. If it is not, step 420, then the program determines whether the singulation mode is in the "PAUSE" state, step 421. If not, the program jumps to decision step 450 (FIG. 4d).

If the singulation mode is "REVERSE", step 420, the timer is decremented, step 422, and the system determines whether the timer is zero, step 423. If not, then the decision block 421 is entered. If the timer is at zero, step 421, the program determines whether the cam switch 30 is off, step 424. If yes (the cam switch 30 is off), the routine jumps to process 200, step 223 (FIG. 3e). If not, the timer is set to forward pulse-time, step 425, the singulation mode is set to "FORWARD", step 426, and the motor 7 is rotated in the forward direction, step 427. The routine then jumps to the process 300, decision step 303 (FIG. 4a).

If the singulation mode is in the pause state, step 421, the timer is decremented, step 428, and the timer is checked,- step 429. If the timer is at zero, step 429, then the system sets the timer to forward-pulse time, step 430, singulation mode is set to "FORWARD", step 431, and the motor 7 is rotated in the forward direction, step 432. The program then jumps to process 300, step 303. (FIG. 4a).

The decision step 450 (FIG. 4d) is entered from decision block 421 (FIG. 4c), as aforementioned, when the singulation mode is in the pause state. If the singulation mode is not at the "NEXT COIL WAIT" state, step 450, the routine jumps to process 300, step 303 (FIG. 4a). If the singulation mode is at the "NEXT COIL WAIT" state, step 450, the system determines whether the cam switch 30 is off, step 451. If cam switch 30 is on, step 451, then the inquiry, step 451, is repeated until switch 30 is turned off, step 451. The timer is set to advance time, step 452, and the singulation mode is set to "FORWARD", step 453. The routine then jumps to the process 300, decision step 303 (FIG. 4a).

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. An interactive system for filling prescriptions at a central, prescription-filling workstation comprising:

a graphical interface and processing means disposed at said central, prescription-filling workstation for monitoring operations of a pharmacy operatively connected thereto, said central, prescription-filling workstation sequentially and interactively prompting an operator to perform appropriate, predetermined steps in filling a prescription at a predetermined inventory location, said graphical interface and processing means comprising means for monitoring the status of at least one drug at said predetermined inventory location and for graphically displaying its status;

storage means for storing a plurality of drugs in predetermined, separately-addressable storage locations, said storage means being operatively connected to said graphical interface and processing means disposed at said central, prescription-filling workstation;

input means operatively connected to said graphical interface and processing means for feeding information representative of said status of said at least one drug and of pharmacy operations into said processing means an array of dispensing cells in communicative relationship with said processing means, each cell comprising its own microprocessor, said microprocessor comprising a computer program for singulating a predetermined pharmaceutical, said computer program adapted to singulate and dispense each respective, predetermined pharmaceutical.

2. The interactive system for filling prescriptions in accordance with claim 1, wherein said processing means comprises a program for monitoring the status of at least one drug at one predetermined location and for graphically displaying said status.

3. The interactive system for fulfilling prescriptions in accordance with claim 2, wherein said program comprises a sequential prompting routine for sequentially prompting said operator at said central, prescription-filling workstation to perform predetermined steps.

4. The interactive system for filling prescriptions in accordance with claim 3, wherein said sequential prompting routine comprises a verification sub-routine for verifying operator completion of previous operational steps.

5. The inter system for filling prescriptions in accordance with claim 3, wherein said sequential prompting routine comprises an identification sub-routine for identifying of an operator, and wherein said sub-routine requires that said operator be identified in order to perform said predetermined steps.

6. The interactive system for filling prescriptions in accordance with claim 5, wherein said system further comprises scanning means connected to said processing means at said central, prescription-filling workstation, for scanning an operator identification badge.

7. The interactive system for filling prescriptions in accordance with claim 2, wherein said program has a processing sub-routine for receiving and processing information fed to said input means that comprises data representative of personnel, activities, and inventory at said central, prescription-filling workstation.

8. The interactive system for filling prescriptions in accordance with claim 2, wherein said program controls said storage means in accordance with input information including at least one of the following:

a) proximity to a predetermined packaging/shipping location;

b) probability of future drug access at a predetermined inventory storage location;

c) size of said separately-addressable storage locations; and d) location of confusingly similar drugs or dosages.

9. The system for filling prescriptions in accordance with claim 1, wherein said separately-addressable storage locations comprise adjustable shelves.

10. The system for filling prescriptions in accordance with claim 1, wherein said separately-addressable storage locations comprises at least one array of dispensing cells.

11. An interactive pharmaceutical dispensing system for filling prescriptions, comprising a central workstation operatively connected to at least one pharmacy, said central workstation comprising a controller computer and a display for monitoring and displaying operations of said at least one pharmacy, said controller computer having a program for sequentially and interactively prompting an operator to perform appropriate, predetermined steps in filling a prescription, said program further comprising a routine for monitoring the status of at least one drug disposed at a predetermined inventory location and for graphically displaying the dispensing status of said at least one drug, said workstation further comprising an array of dispensing cells, each comprising its own microprocessor, said dispensing cells each receiving a bulk loading of a particular drug, and each including singulating and dispensing means for dispensing a quantity of said drug under the control of its own microprocessor.

12. The interactive pharmaceutical dispensing system for filling prescriptions in accordance with claim 11, wherein each dispensing cell of said array of dispensing cells is identified by a predetermined, separately-addressable storage location.

13. The interactive pharmaceutical dispensing system for filling prescriptions in accordance with claim 12, wherein each of said dispensing cells of said array of dispensing cells comprises singulation means for dispensing an accurate count of a drug.

14. The interactive pharmaceutical dispensing system for filling prescriptions in accordance with claim 11, wherein said display comprises a graphical interface for displaying said status of said at least one drug and of pharmacy operations.

15. The interactive pharmaceutical dispensing system for filling prescriptions in accordance with claim 11, wherein said program for sequential prompting comprises a verification subroutine for verifying operator completion of previous operational steps.

16. The interactive pharmaceutical dispensing system for filling prescriptions in accordance with claim 11, wherein said program for sequential prompting comprises an identification subroutine for identifying an operator, and wherein said subroutine requires that said operator be identified in order to perform predetermined steps.

17. The interactive pharmaceutical dispensing system for filling prescriptions in accordance with claim 11, wherein said system further comprises means for scanning an operator identification badge.

18. An interactive pharmaceutical dispensing system for filling prescriptions, comprising a central workstation operatively connected to at least one pharmacy, said central workstation comprising an array of prescription filling modules each having its own microprocessor for controlling each prescription filling cell, and a central computer operatively connected to said array, for sequentially and interactively prompting an operator at said central workstation to perform appropriate, predetermined steps in filling a prescription ordered by said at least one pharmacy, each of said cells having means for receiving a bulk loading of a particular drug and programming means for singulating, dispensing and monitoring a given quantity of said drug.

19. The interactive pharmaceutical dispensing system for filling prescriptions in accordance with claim 18, wherein said programming means include a program having a routine for sequential prompting said operator to perform prescription filling steps.

20. The interactive pharmaceutical dispensing system for filling prescriptions in accordance with claim 19, wherein said program for sequential prompting comprises an identification subroutine for identifying an operator, and wherein said subroutine requires that said operator be identified in order to perform predetermined steps.

21. The interactive pharmaceutical dispensing system for filling prescriptions in accordance with claim 18, wherein each dispensing cell of said array of dispensing cells is identified by a predetermined, separately-addressable storage location.

22. The interactive pharmaceutical dispensing system for filling prescription, in accordance with claim 18, wherein each of said dispensing cells of said array of dispensing cells comprises singulation means for dispensing an accurate count of a drug.

23. The interactive pharmaceutical dispensing system for filling prescriptions in accordance with claim 18, further comprising a display having a graphical interface for displaying status of at least one prescription, and of pharmacy operations.

24. The interactive pharmaceutical dispensing system for filling prescriptions in accordance with claim 18, wherein said program includes a verification subroutine for verifying operation completion of previous operational steps.

25. The interactive pharmaceutical dispensing system for filling prescriptions in accordance with claim 18, wherein said system further comprises scanning means operatively connected to said central computer for scanning an operator identification badge.

* * * * *